(12) United States Patent
Tabata et al.

(10) Patent No.: US 10,156,510 B2
(45) Date of Patent: Dec. 18, 2018

(54) PARTICLE IMAGING APPARATUS AND PARTICLE IMAGING METHOD

(71) Applicant: Sysmex Corporation, Kobe-shi, Hyogo (JP)

(72) Inventors: Seiichiro Tabata, Kobe (JP); Masaki Ishisaka, Kobe (JP); Kenji Akama, Kobe (JP); Yoshinobu Miura, Kobe (JP); Masatoshi Yanagida, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 15/443,865

(22) Filed: Feb. 27, 2017

(65) Prior Publication Data

US 2017/0227446 A1    Aug. 10, 2017

Related U.S. Application Data

(63) Continuation of application No. PCT/JP2015/071727, filed on Jul. 30, 2015.

(30) Foreign Application Priority Data

Aug. 28, 2014 (JP) .................................. 2014-173642
May 20, 2015 (JP) .................................. 2015-103253

(51) Int. Cl.
   *G01N 15/14* (2006.01)
   *G01N 21/05* (2006.01)
   *G01N 15/10* (2006.01)

(52) U.S. Cl.
   CPC ......... *G01N 15/1434* (2013.01); *G01N 21/05* (2013.01); *G01N 2015/1006* (2013.01)

(58) Field of Classification Search
   CPC ............... G01N 15/14; G01N 15/1404; G01N 15/1434; G01N 15/1436; G01N 2015/144;

(Continued)

(56) References Cited

U.S. PATENT DOCUMENTS 5,690,895 A * 11/1997 Matsumoto ........ G01N 15/1404
                                                                356/246
8,573,060 B2   11/2013 Huang et al.
   (Continued)

FOREIGN PATENT DOCUMENTS

JP        S63-94156 A     4/1988
JP        01-313758 A    12/1989
   (Continued)

OTHER PUBLICATIONS

Arakawa, T., "Development of Micro Fluidic Systems for Biomolecular Analysis", *Waseda University*, Mar. 2007, 43 pages. (with English language translation).

(Continued)

*Primary Examiner* — John Lee
(74) *Attorney, Agent, or Firm* — Brinks Gilson & Lione

(57) ABSTRACT

A particle imaging apparatus comprises a flow path comprising a first flow path section, a second flow path section connected downstream of the first flow path section, and a third flow path section that is branched from the first flow path section, a particle detection unit comprising a light source and a light detector, a particle sorting unit configured to adjust a flow direction of the particle, and a particle imaging unit configured to take an image of a particle that flows in the second flow path section. The flow path is structured such that a cross-sectional area of the second flow path section is greater than a cross-sectional area of the first flow path section. The first flow path section and the second flow path section are disposed so as to be linearly aligned.

20 Claims, 25 Drawing Sheets

EMBODIMENT 1

(58) Field of Classification Search
CPC ........... G01N 15/1456; G01N 15/1459; G01N 15/147; G01N 2015/149; G01N 2015/1006; G01N 15/10; G01N 21/05
See application file for complete search history.

(56) References Cited

U.S. PATENT DOCUMENTS

| | | |
|---|---|---|
| 2004/0069717 A1 | 4/2004 | Laurell et al. |
| 2007/0020721 A1 | 1/2007 | Yoshida et al. |
| 2008/0213821 A1 | 9/2008 | Liu et al. |
| 2008/0218753 A1 | 9/2008 | Chang et al. |
| 2008/0234984 A1 | 9/2008 | Ortyn et al. |
| 2008/0261295 A1 | 10/2008 | Butler et al. |
| 2009/0117664 A1 | 5/2009 | Shinoda |
| 2009/0178716 A1 | 7/2009 | Kaduchak et al. |
| 2012/0122084 A1 | 5/2012 | Wagner et al. |
| 2012/0315690 A1* | 12/2012 | Di Carlo ........... B01L 3/502746 435/287.1 |
| 2013/0083315 A1* | 4/2013 | Lo ............................ G01J 3/46 356/73 |
| 2013/0167958 A1* | 7/2013 | Prakash .............. F16K 99/0001 137/597 |
| 2013/0258075 A1 | 10/2013 | Muraki et al. |
| 2014/0273067 A1* | 9/2014 | Wanders ............ G01N 33/5094 435/29 |
| 2015/0132766 A1 | 5/2015 | Yasuda et al. |
| 2016/0340636 A1* | 11/2016 | Tabata ..................... G01N 1/40 |

FOREIGN PATENT DOCUMENTS

| | | |
|---|---|---|
| JP | H05-296915 A | 11/1993 |
| JP | H06-281558 A | 10/1994 |
| JP | 2898321 B | 3/1999 |
| JP | 2004-534206 | 11/2004 |
| JP | 2004-535912 A | 12/2004 |
| JP | 2007-024844 A | 2/2007 |
| JP | 2007-504446 A | 3/2007 |
| JP | 4018063 B | 9/2007 |
| JP | 2008-533440 A | 8/2008 |
| JP | 2010-151832 A | 7/2010 |
| JP | 2010-525325 A | 7/2010 |
| JP | 2011-510299 A | 3/2011 |
| JP | 2012-523572 A | 10/2012 |
| JP | 2013-513109 A | 4/2013 |
| JP | 5364725 B | 9/2013 |
| JP | 2013-210270 A | 10/2013 |
| JP | 2013-242335 A | 12/2013 |
| JP | 2014-503195 A | 2/2014 |
| WO | WO02/054339 A1 | 7/2002 |
| WO | WO 2009/139246 A1 | 11/2009 |
| WO | WO 2013/147114 A1 | 10/2013 |

OTHER PUBLICATIONS

Huang, N.T. et al., "Recent Advancements in Optofluidics-Based Single-Cell Analysis: Optical On-Chip Cellular Manipulation, Treatment and Property Detection" *Lab on a Chip*, vol. 14, No. 7, Apr. 7, 2014, pp. 1230-1245.

* cited by examiner

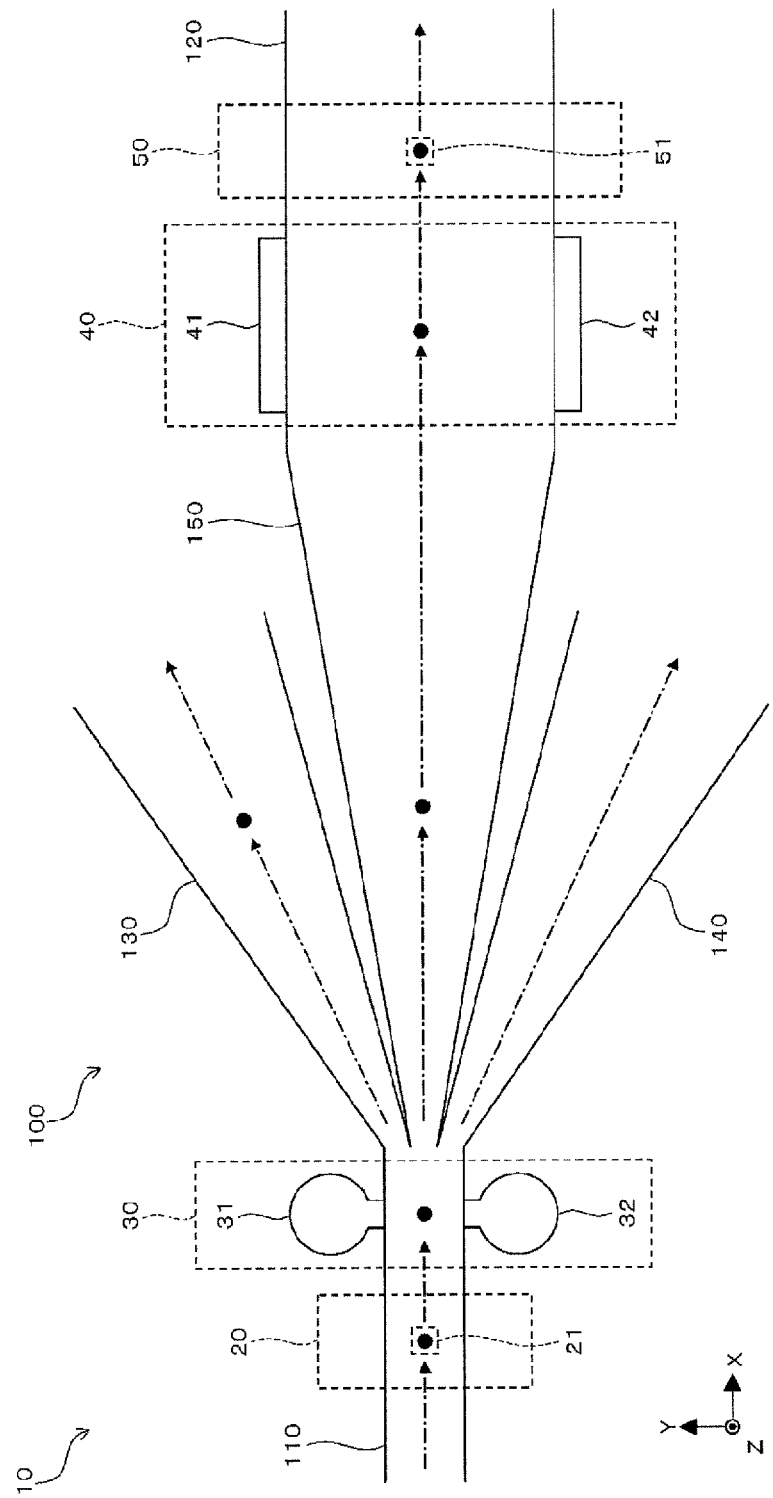

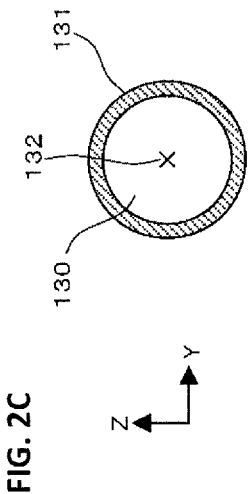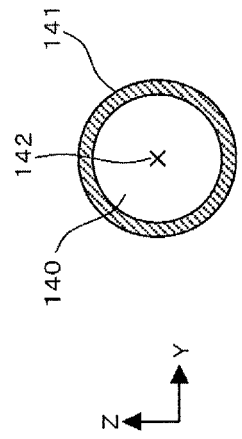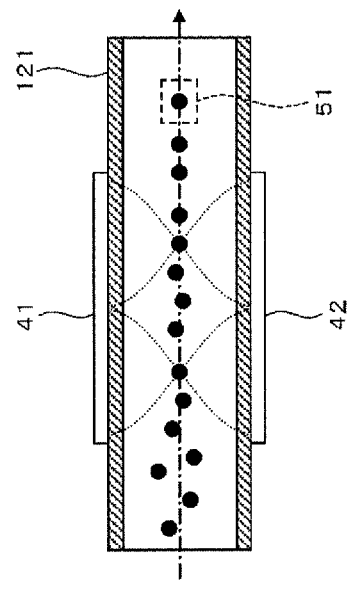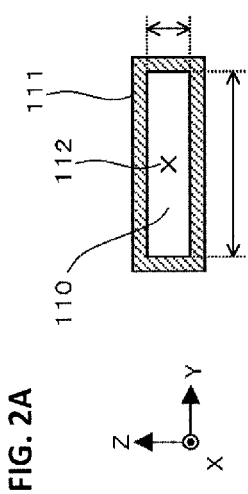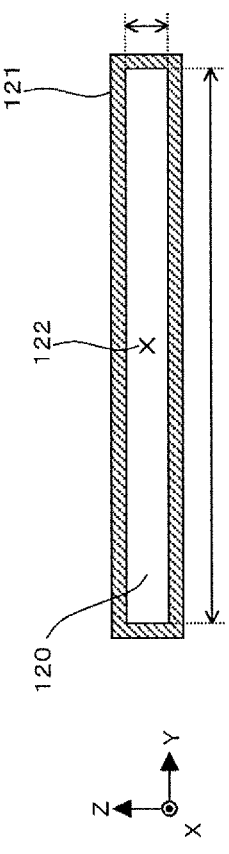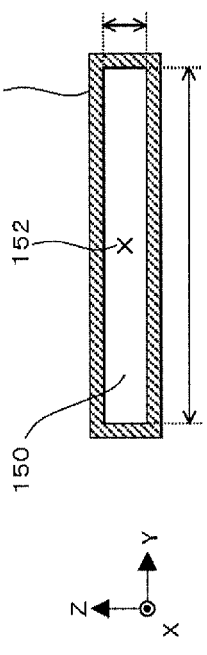
FIG. 2A  FIG. 2C
FIG. 2B  FIG. 2D
FIG. 2E  FIG. 2F FIG. 7A  EMBODIMENT 2
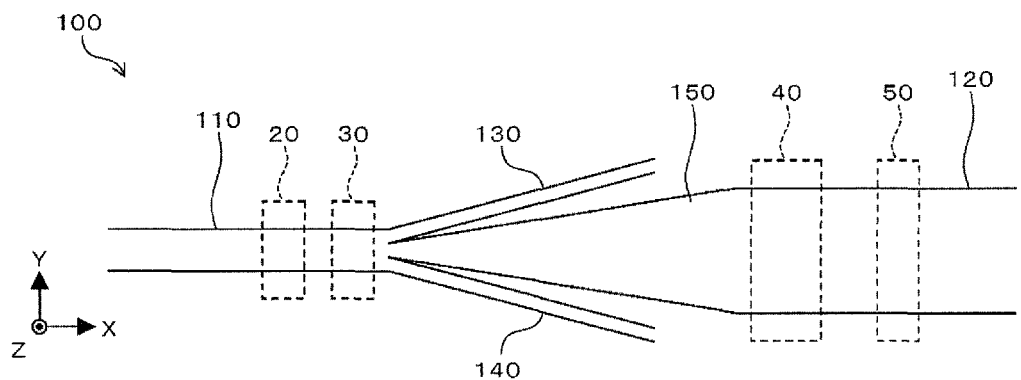
FIG. 7B  EMBODIMENT 3
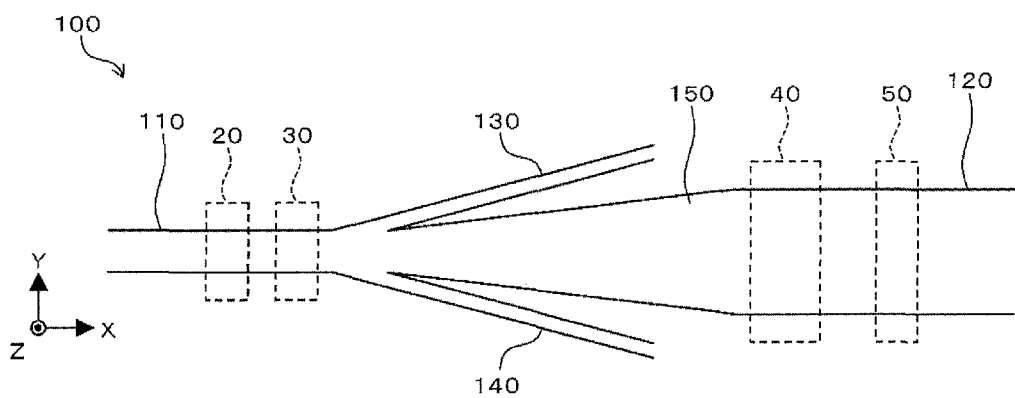
FIG. 7C  EMBODIMENT 4
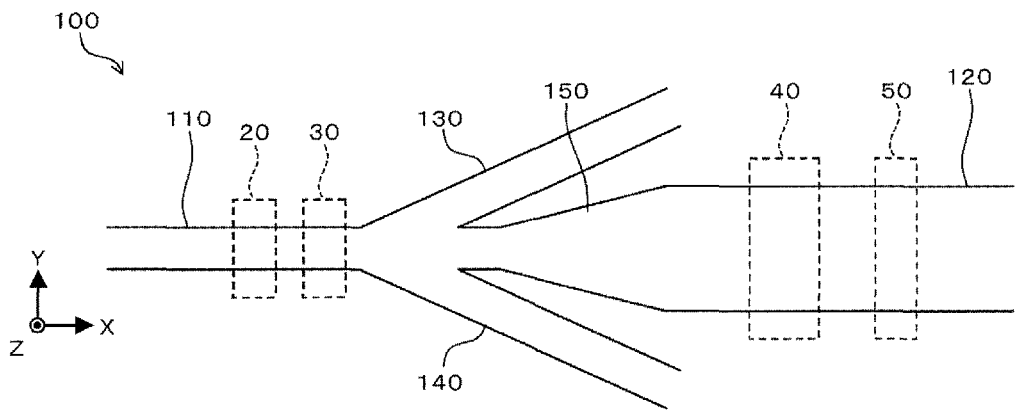

FIG. 8A   EMBODIMENT 5
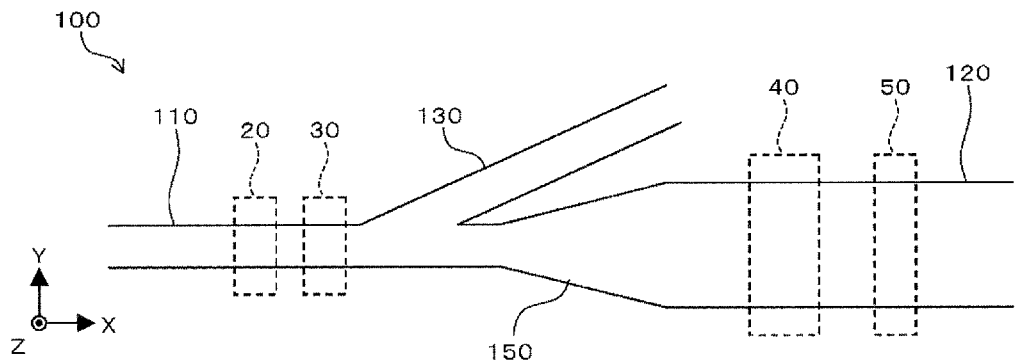
FIG. 8B   EMBODIMENT 6
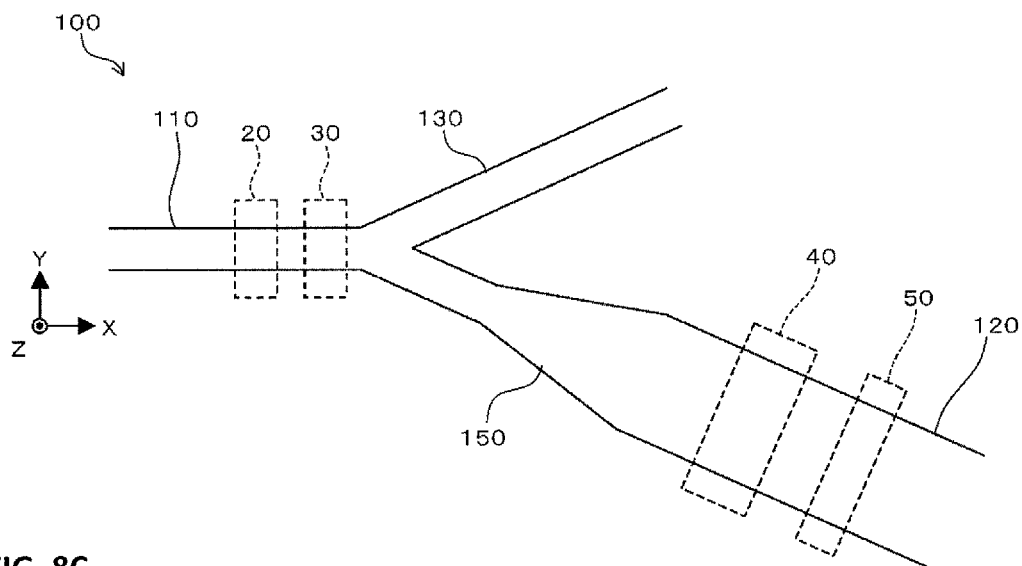
FIG. 8C
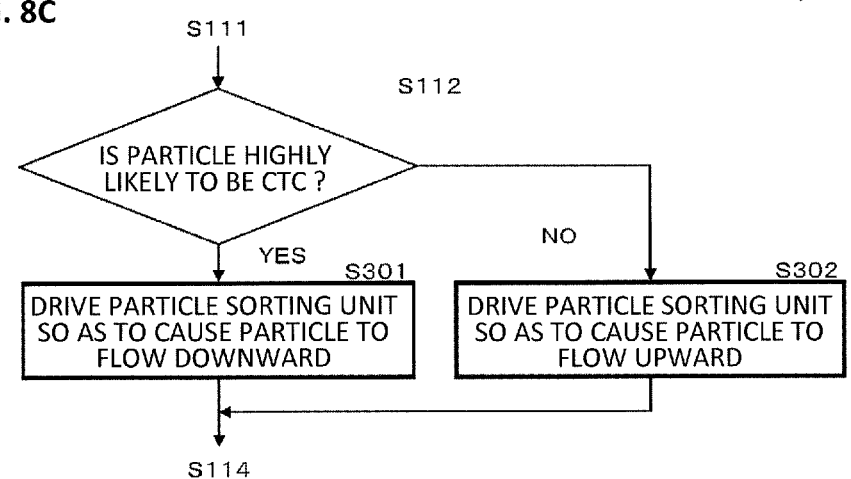

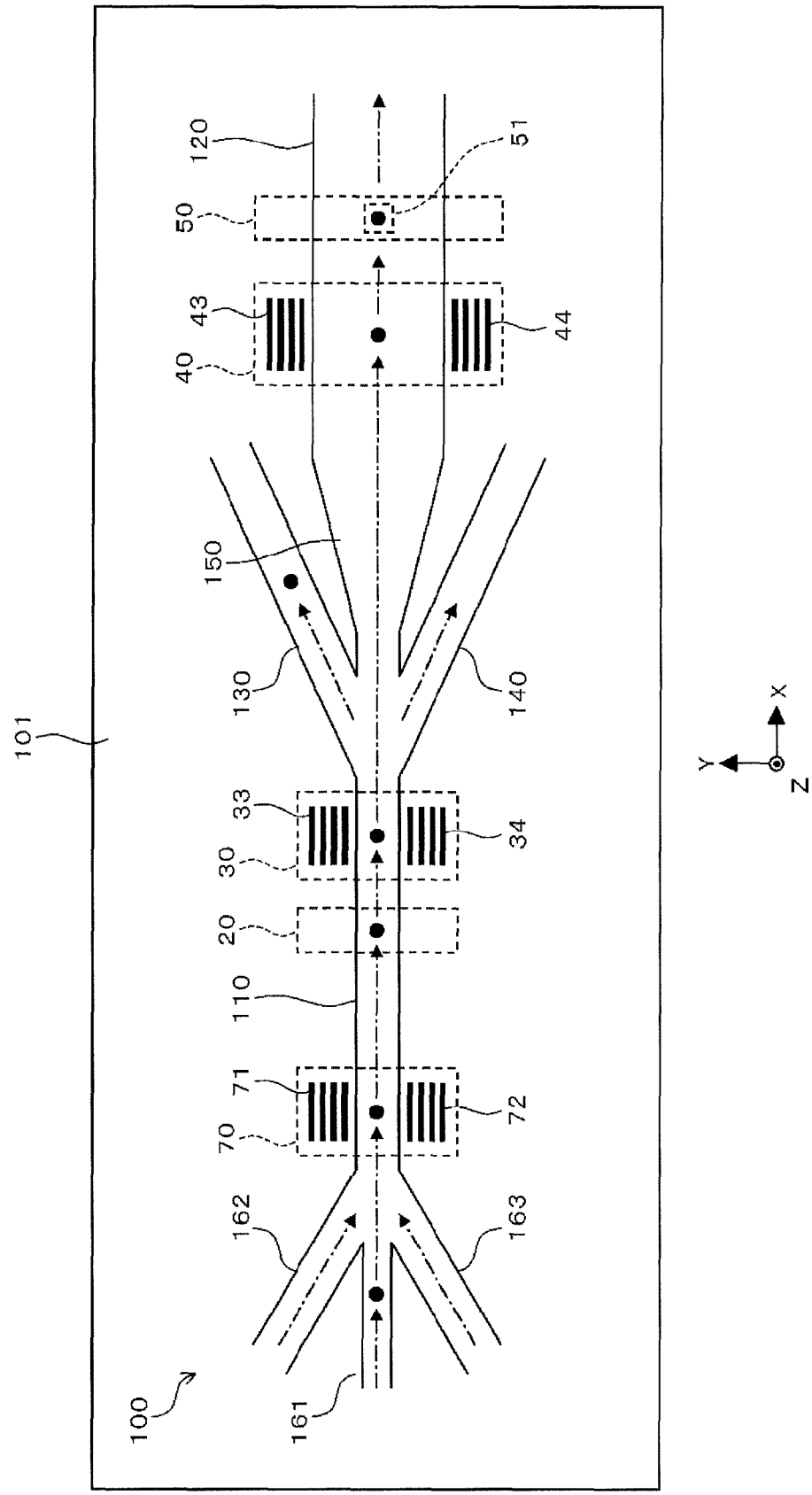

FIG. 12A  EMBODIMENT 8
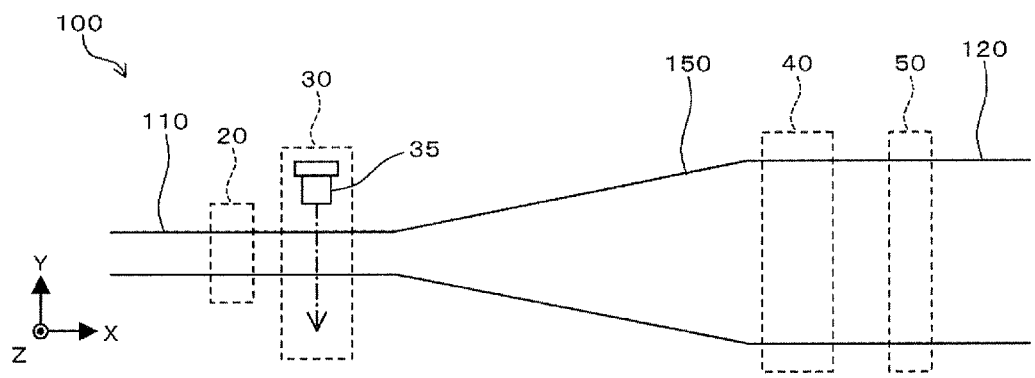
FIG. 12B
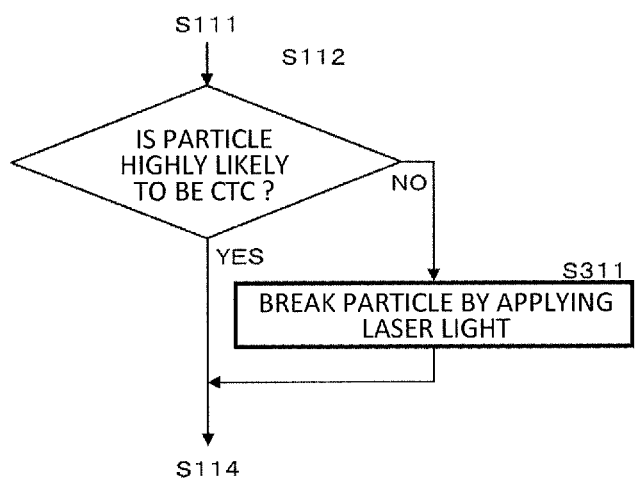

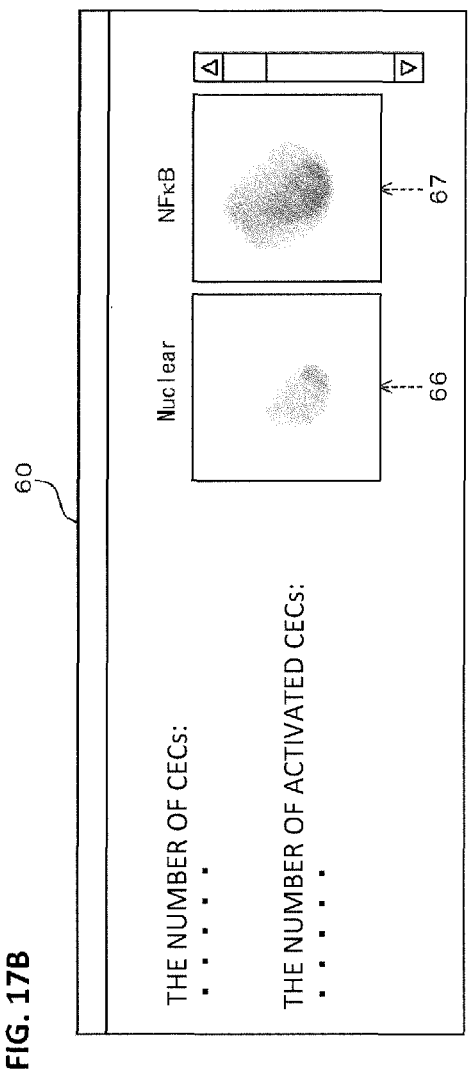
FIG. 17B
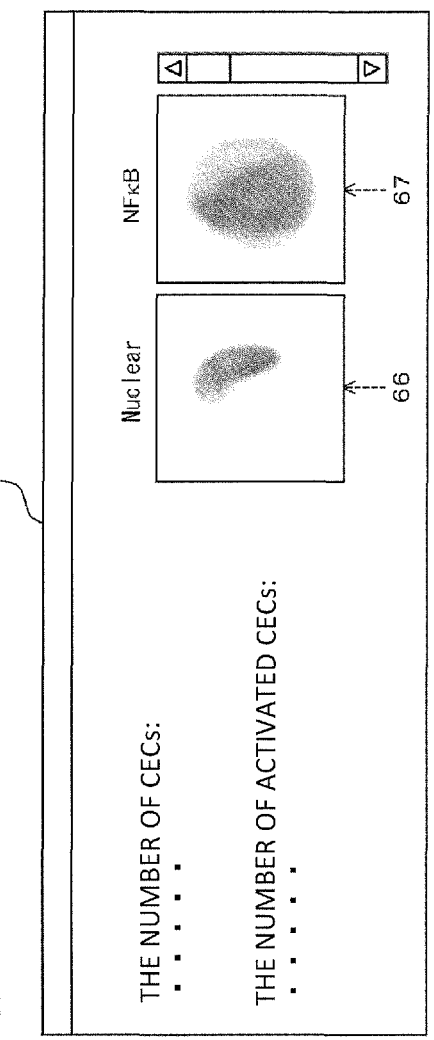
FIG. 17C
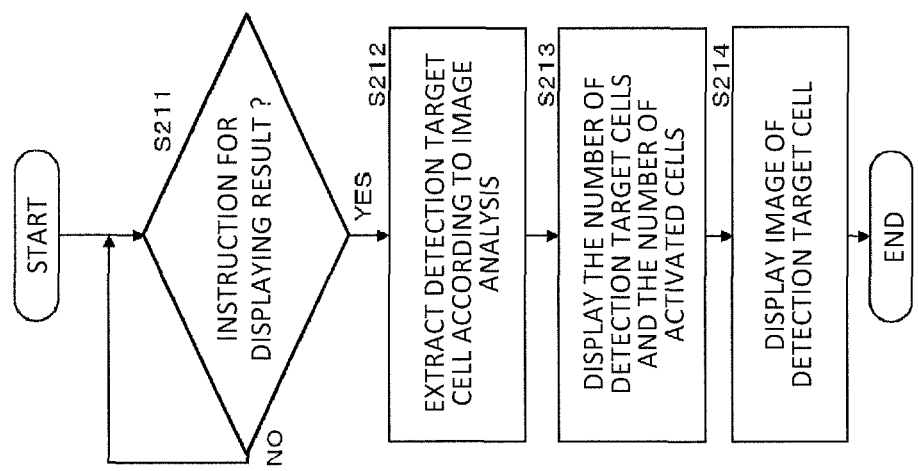
FIG. 17A EMBODIMENT 13

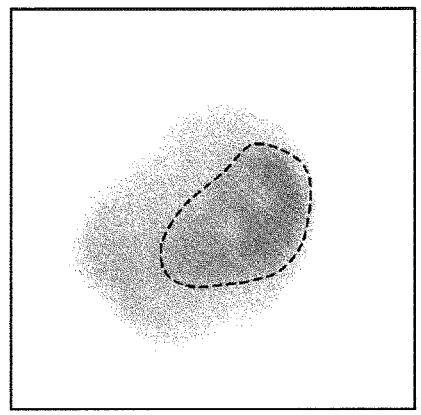
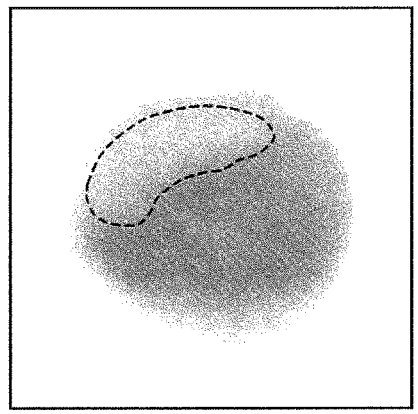
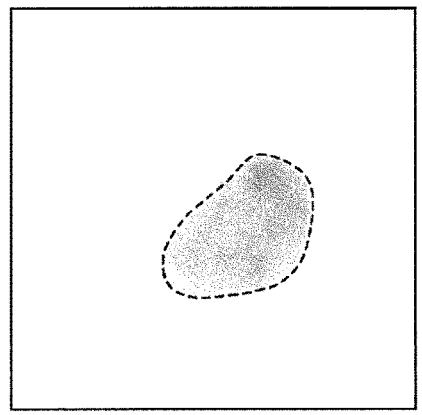
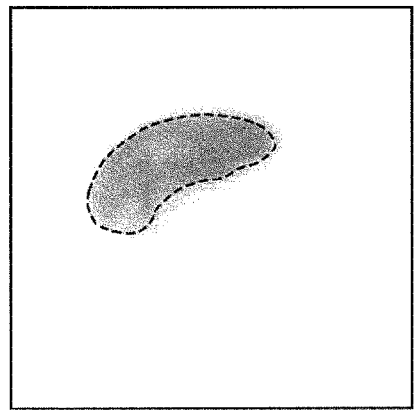
FIG. 18A ACTIVATED
FIG. 18B UNACTIVATED

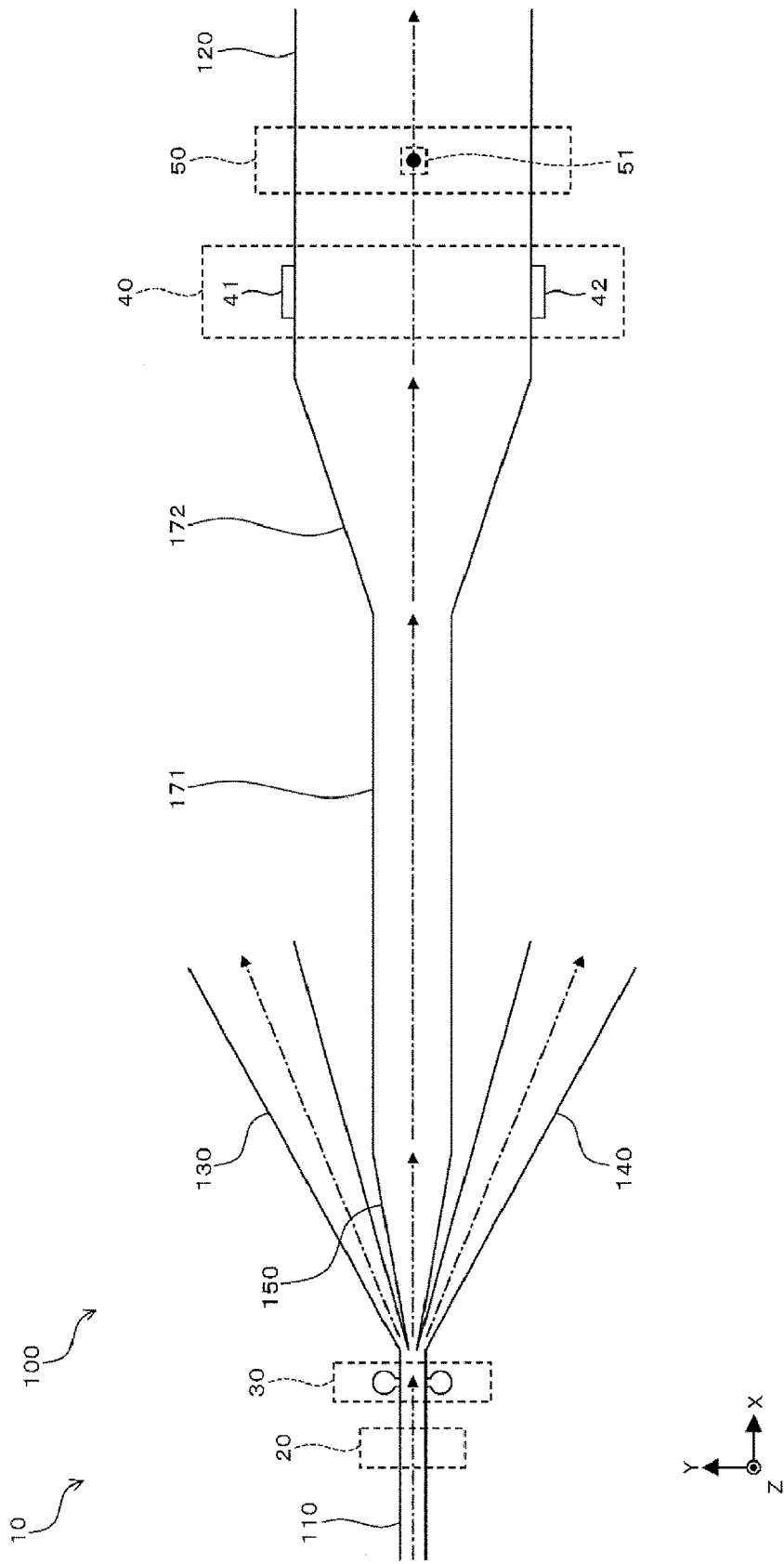

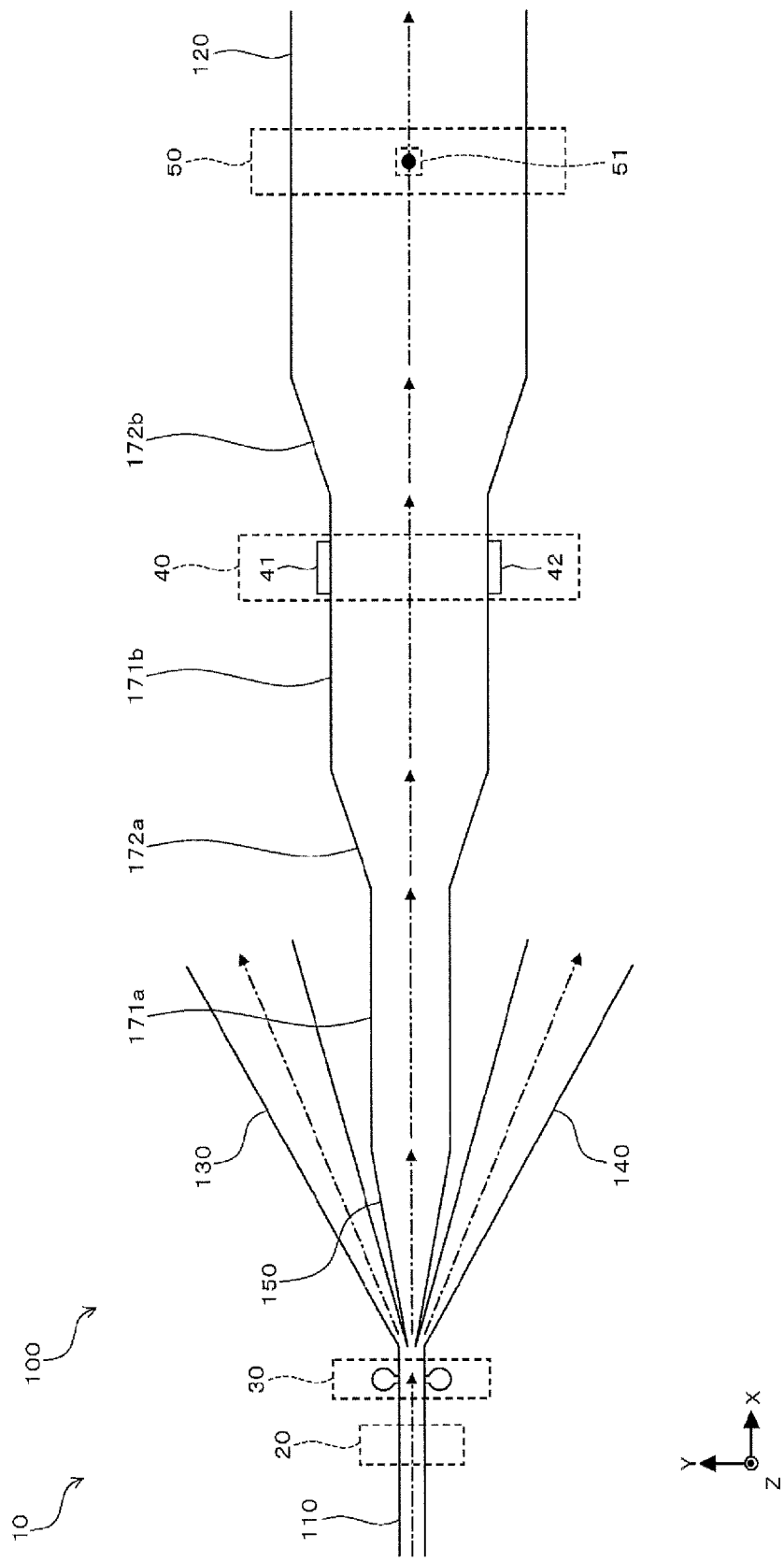

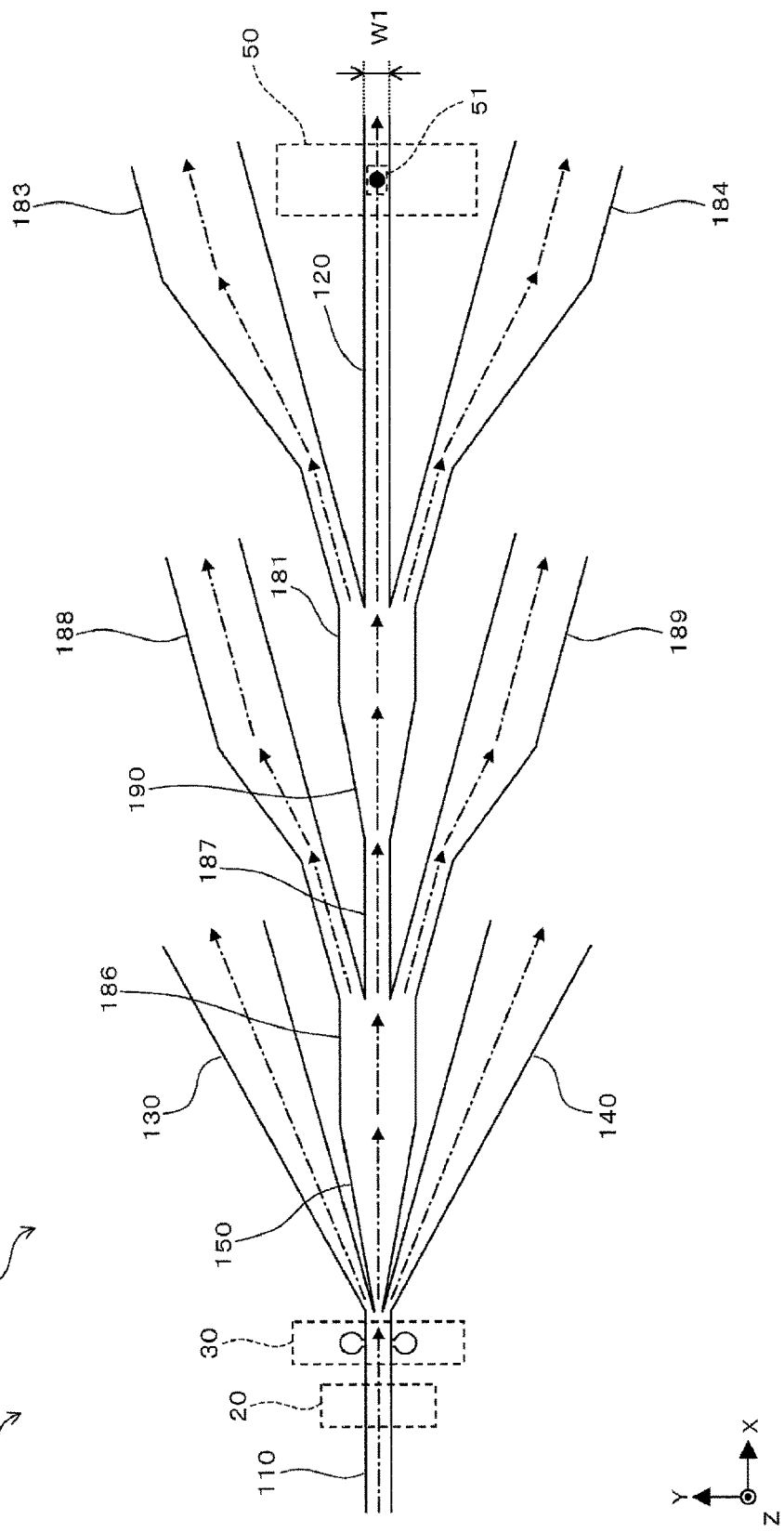

PARTICLE IMAGING APPARATUS AND PARTICLE IMAGING METHOD

RELATED APPLICATIONS

This application is a continuation application of PCT/JP2015/071727 having an international filing date of Jul. 30, 2015, which claims priority to JP2014-173642 filed Aug. 28, 2014 and JP2015-103253 filed May 20, 2015. The entire contents of these applications are incorporated herein by reference.

BACKGROUND OF THE INVENTION

1. Field of the Invention

The present invention relates to a particle imaging apparatus and a particle imaging method.

2. Description of the Related Art

As a specimen measurement apparatus using a flow cytometer, an apparatus that includes a particle detection unit that detects a particle in a measurement sample that flows in a flow cell, and an imaging unit that takes an image of the particle in the measurement sample that flows in the flow cell, is known. For example, in the specimen measurement apparatus disclosed in Patent Literature 1, a structure for taking an image of a cell is disposed downstream of a cell detection unit. The specimen measurement apparatus applies laser light to a cell in a measurement sample that flows in a flow cell, and takes an image of the cell in the measurement sample by a CCD camera by using, as a trigger, a signal emitted from the cell.

CITATION LIST

Patent Literature

[PTL 1] Japanese Laid-Open Patent Publication No. S63-94156

SUMMARY OF THE INVENTION

Problems to be Solved by the Invention

In the above structure, if a speed at which a particle flows in the flow cell is reduced in order to enhance the quality of a particle image, when it is desired to take images of a very few amount of cells included in a measurement sample, for example, one cell in hundreds of thousands of cells, a large amount of measurement sample needs to be measured. This causes a problem that time for taking images of the cells becomes very long.

Solution to the Problems

A particle imaging apparatus according to a first aspect of the present invention includes: a flow path comprising a first flow path section, a second flow path section connected downstream of the first flow path section, and a third flow path section that is branched from the first flow path section, between the first flow path section and the second flow path section, the flow path configured to cause a measurement sample including particles to flow, a particle detection unit comprising a light source configured to apply light to a particle that flows in the first flow path section, and a light detector that receives light generated from the particle by application of the light, a particle sorting unit configured to adjust a flow direction of the particle flowing in the first flow path section such that the flow direction is selected from among at least a direction toward the second flow path section and a direction toward the third flow path section, based on an intensity of the light received by the light detector, and a particle imaging unit configured to take an image of a particle that flows in the second flow path section. The flow path is structured such that a cross-sectional area of the second flow path section is greater than a cross-sectional area of the first flow path section. The first flow path section and the second flow path section are disposed so as to be linearly aligned.

A particle imaging method according to a second aspect of the present invention includes: causing a measurement sample to flow in a flow path which comprises a first flow path section, a second flow path section connected downstream of the first flow path section, and a third flow path section that is branched from the first flow path section, between the first flow path section and the second flow path section, the flow path being structured such that a cross-sectional area of the second flow path section is greater than a cross-sectional area of the first flow path section, and the first flow path section and the second flow path section are linearly aligned, applying light to a particle in the measurement sample that flows at a first speed, and detecting light generated from the particle, adjusting a direction in which the particle in the measurement sample flows, based on an intensity of the detected light, and taking an image of a particle in the measurement sample that flows in the second flow path section at a second speed lower than the first speed.

A particle imaging apparatus according to a third aspect of the present invention includes: a flow path comprising a first flow path section, a second flow path section connected downstream of the first flow path section, and a third flow path section that is branched from the first flow path section, between the first flow path section and the second flow path section, the flow path configured to cause a measurement sample including particles to flow, a particle detection unit comprising a light source that applies light to a particle that flows in the first flow path section, and a light detector that receives light generated from the particle by application of the light, a particle sorting unit configured to adjust a flow direction of the particle flowing in the first flow path section such that the flow direction is selected from among at least a direction toward the second flow path section and a direction toward the third flow path section, based on an intensity of the light received by the light detector, and a particle imaging unit configured to take an image of a particle that flows in the second flow path section. The third flow path section has a cross-sectional area that is gradually increased from an upstream side of the flow path toward a downstream side thereof.

Advantageous Effects of the Invention

According to the present invention, time for obtaining images of a cell can be shortened.

BRIEF DESCRIPTION OF THE DRAWINGS

FIG. 1 is a schematic diagram illustrating a configuration of a particle imaging apparatus according to Embodiment 1 as viewed in the Z-axis negative direction.

FIG. 2A to FIG. 2F are schematic diagrams illustrating cross-sections of a first flow path section, a second flow path section, a third flow path section, a fourth flow path section, and a fifth flow path section according to Embodiment 1, and a schematic diagram illustrating forming of an ultrasonic standing wave according to Embodiment 1.

FIGS. 7A to 7C are schematic diagrams illustrating flow paths according to Embodiments 2 to 4, respectively.

FIGS. 8A and 8B are schematic diagrams illustrating flow paths according to Embodiments 5 and 6, respectively, and FIG. 8C is a flow chart showing a process performed by a particle imaging apparatus according to Embodiment 6.

FIG. 9 is a schematic diagram illustrating a flow path according to Embodiment 7.

FIG. 12A is a schematic diagram illustrating a flow path according to Embodiment 8, and FIG. 12B is a flow chart showing a process performed by a particle imaging apparatus according to Embodiment 8.

FIG. 17A is a flow chart showing a display process performed by a particle imaging apparatus according to Embodiment 13, and FIGS. 17B and 17C illustrate screens to be displayed on an output unit according to Embodiment 13.

FIG. 18A illustrates examples of taken images of fluorescence of each of a nucleus and a signaling molecule in an activated vascular endothelial cell according to Embodiment 13, and FIG. 18B illustrates examples of taken images of fluorescence of each of a nucleus and a signaling molecule in an unactivated vascular endothelial cell according to Embodiment 13.

FIG. 19 is a schematic diagram illustrating a configuration of a particle imaging apparatus according to Embodiment 14 as viewed in the Z-axis negative direction.

FIG. 20 is a schematic diagram illustrating a configuration of a particle imaging apparatus according to modification of Embodiment 14 as viewed in the Z-axis negative direction.

FIG. 25 is a schematic diagram illustrating a configuration of a particle imaging apparatus according to another modification of Embodiment 15 as viewed in the Z-axis negative direction. The drawings are exclusively for explanation and are not intended to limit the scope of the present invention.

DETAILED DESCRIPTION OF THE PREFERRED EMBODIMENTS

Figure 3B:
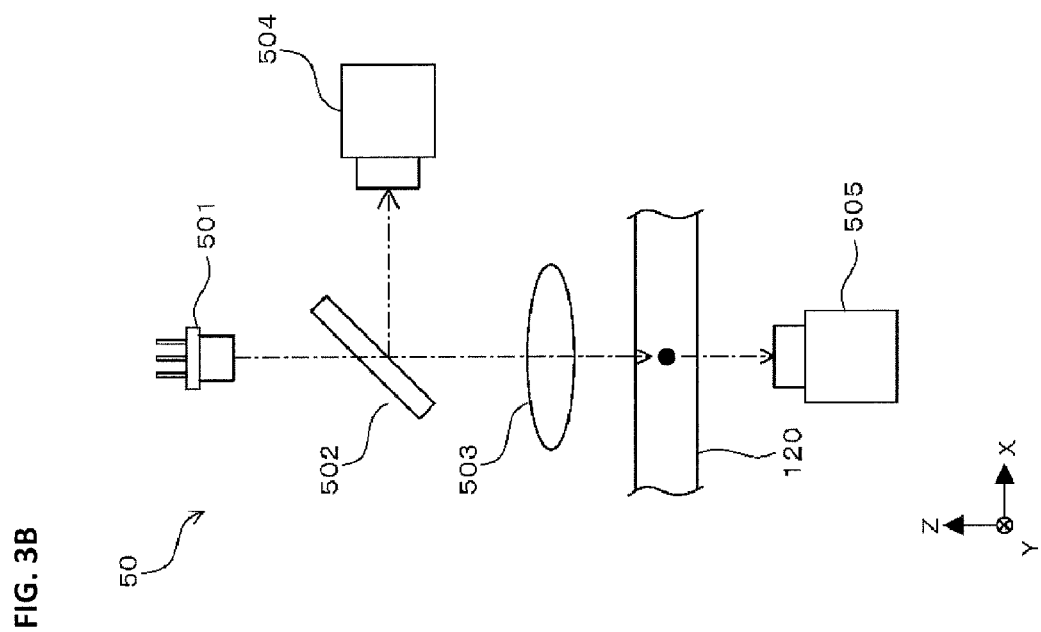
FIG. 3B is a schematic diagram illustrating a particle imaging unit according to Embodiment 1 as viewed in the Y-axis positive direction.

In Embodiments 1 to 12 described below, the present invention is applied to an apparatus for taking an image of a circulating tumor cell included in a blood specimen. Hereinafter, a circulating tumor cell is referred to as a CTC (Circulating Tumor Cell). Advanced cancer cells circulate in flowing blood or lymph, and metastasize to a distant organ. It is acknowledged that a CTC in blood is useful for therapeutic effect determination and as a prognosis-predicting factor for patients of metastatic cancers such as breast cancer, prostate cancer, and colorectal cancer. Measurement of a CTC is effective for determining an effect of a treatment, or predicting prognosis such as a progression-free survival rate, an overall survival rate, or the like. The amount of CTCs circulating in blood is very small, and is approximately several CTCs to several tens of CTCs in 10 mL of blood. In the present invention, an imaging target is not limited to a CTC, and may be another cell included in a blood specimen.

°Embodiment 1<

As shown in FIG. 1, a particle imaging apparatus 10 includes a flow path 100, a particle detection unit 20, a particle sorting unit 30, a particle alignment unit 40, and a particle imaging unit 50. For convenience, in FIG. 1, XYZ coordinate axes orthogonal to each other are indicated.

The flow path 100 includes a first flow path section 110, a second flow path section 120, a third flow path section 130, a fourth flow path section 140, and a fifth flow path section 150. Each of the flow path sections is formed from glass or synthetic resin having translucency. A measurement sample 12 including particles flows in the flow path 100. The measurement sample 12 is prepared based on a blood specimen 11 as described below with reference to FIG. 4. In the flow path 100, the X-axis negative side is the upstream side, and the X-axis positive side is the downstream side.

The first flow path section 110 and the second flow path section 120 are disposed so as to be linearly aligned. The second flow path section 120 is connected through the fifth flow path section 150 to the downstream side portion of the first flow path section 110, that is, to the X-axis positive side portion of the first flow path section 110. The third flow path section 130 and the fourth flow path section 140 are branched from the first flow path section 110, between the first flow path section 110 and the second flow path section 120. The downstream side portion of the second flow path section 120, the downstream side portion of the third flow path section 130, and the downstream side portion of the fourth flow path section 140 are open to the atmosphere, and connected to not-illustrated waste liquid storing units.

As shown in FIG. 2A, the first flow path section 110 is formed as a space surrounded by a member 111. A central axis 112 of the first flow path section 110 extends in the X-axis direction. The first flow path section 110 has a rectangular cross-sectional shape, and, on the cross-section of the first flow path section 110, the width in the Y-axis direction is greater than the width in the Z-axis direction. The first flow path section 110 has a constant cross-sectional area.

As shown in FIG. 2B, the second flow path section 120 is formed as a space surrounded by a member 121. A central axis 122 of the second flow path section 120 extends in the X-axis direction. The central axis 122 is on the extension line of the central axis 112. The second flow path section 120 has a rectangular cross-sectional shape, and, on the cross-section of the second flow path section 120, the width in the Y-axis direction is greater than the width in the Z-axis direction. The width in the Z-axis direction on the cross-section of the second flow path section 120 is equal to the width in the Z-axis direction on the cross-section of the first flow path section 110. The width in the Y-axis direction on the cross-section of the second flow path section 120 is greater than the width in the Y-axis direction on the cross-section of the first flow path section 110. The second flow path section 120 has a constant cross-sectional area. The cross-sectional area of the second flow path section 120 is greater than the cross-sectional area of the first flow path section 110.

As shown in FIG. 2C, the third flow path section 130 is formed as a space surrounded by a member 131. A central axis 132 of the third flow path section 130 is tilted relative to the X-axis direction on the X-Y plane. The third flow path section 130 has a round cross-sectional shape. The cross-sectional area of the third flow path section 130 is gradually increased from the upstream side of the flow path 100 toward the downstream side thereof, that is, along the central axis 132 in the X-axis positive direction.

As shown in FIG. 2D, the fourth flow path section 140 is formed as a space surrounded by a member 141. A central axis 142 of the fourth flow path section 140 is tilted relative to the X-axis direction on the X-Y plane. The fourth flow path section 140 has a round cross-sectional shape. The cross-sectional area of the fourth flow path section 140 is gradually increased from the upstream side of the flow path 100 toward the downstream side thereof, that is, along the central axis 142 in the X-axis positive direction. As shown in FIG. 1, the third flow path section 130 and the fourth flow path section 140 are symmetric about the central axis 112 of the first flow path section 110.

As shown in FIG. 2E, the fifth flow path section 150 is formed as a space surrounded by a member 151. A central axis 152 of the fifth flow path section 150 extends in the X-axis direction. The central axis 152 is on the extension line of the central axis 122. The fifth flow path section 150 has a rectangular cross-sectional shape. The width in the Z-axis direction on the cross-section of the fifth flow path section 150 is equal to the width in the Z-axis direction on the cross-section of the first flow path section 110. The cross-sectional area of the fifth flow path section 150 is gradually increased along the central axis 152 in the X-axis positive direction.

Returning to FIG. 1, the measurement sample 12 flows from the upstream side of the first flow path section 110 in a state where the measurement sample 12 is surrounded by a sheath liquid. Particles included in the measurement sample 12 flow in the first flow path section 110 along the central axis 112 in a state where the particles are aligned in line. The particle detection unit 20 applies light to a light application position 21 in the first flow path section 110, and receives light generated from a particle at the light application position 21, to detect the particle.

Figure 3A:
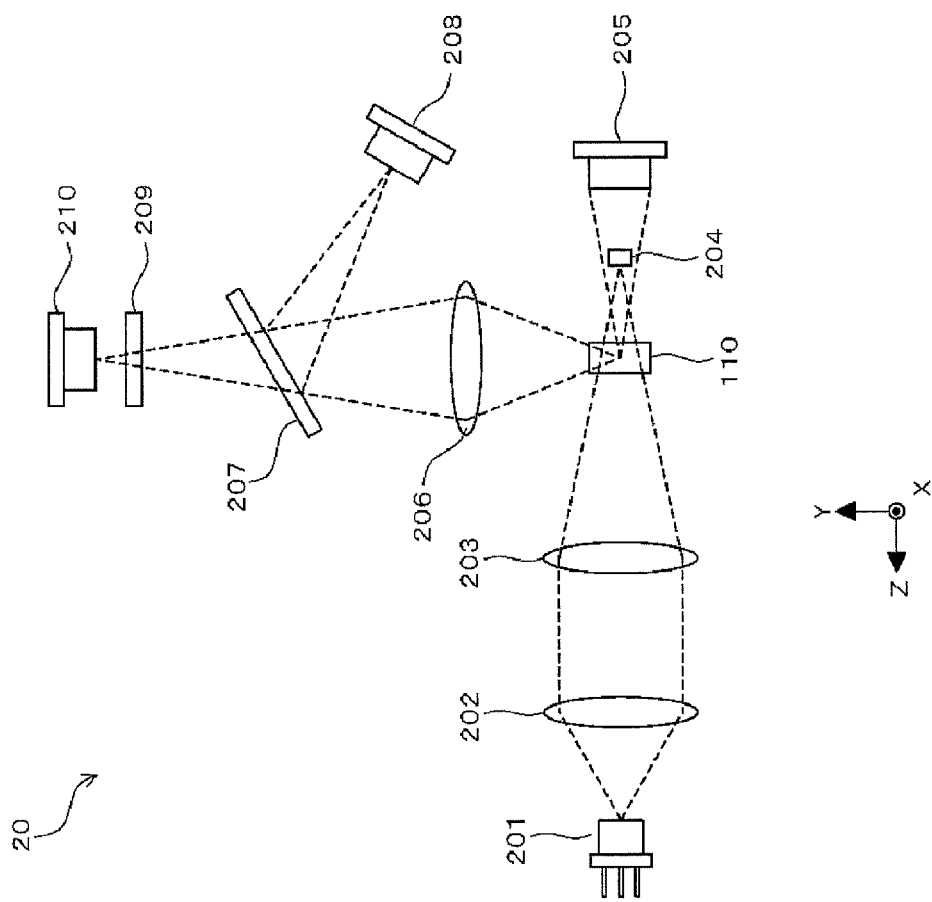
FIG. 3A is a schematic diagram illustrating a particle detection unit according to Embodiment 1 as viewed in the X-axis negative direction.

As shown in FIG. 3A, the particle detection unit 20 includes a light source 201, a collimator lens 202, a condenser lens 203, a beam stopper 204, a light detector 205, a condenser lens 206, a dichroic mirror 207, a light detector 208, a spectral filter 209, and a light detector 210.

Light emitted from the light source 201 is laser light in a red wavelength band. The light emitted from the light source 201 is converted into parallel light by the collimator lens 202. The parallel light obtained by the conversion is condensed by the condenser lens 203. The condensed light is applied to a particle positioned at the light application position 21 shown in FIG. 1. Thus, forward scattered light, side scattered light, and fluorescence are generated. The forward scattered light represents information concerning the size of the particle. The side scattered light represents information of the inside of the particle. The fluorescence represents a degree of staining of the particle. Of the light applied to the light application position 21, light that has not been applied to the particle and has been transmitted through the first flow path section 110 is blocked by the beam stopper 204.

The light detector 205 receives the forward scattered light. The light detector 205 is a photodiode, and outputs an electrical signal based on the received forward scattered light, that is, outputs a forward scattered light signal. The condenser lens 206 condenses the side scattered light and the fluorescence. The dichroic mirror 207 reflects the side scattered light, and allows the fluorescence to transmit therethrough. The light detector 208 receives the side scattered light. The light detector 208 is a photodiode, and outputs an electrical signal based on the received side scattered light, that is, outputs a side scattered light signal. The spectral filter 209 allows the fluorescence to transmit therethrough. The light detector 210 receives the fluorescence. The light detector 210 is an avalanche photodiode, and outputs an electrical signal based on the received fluorescence, that is, outputs a fluorescence signal.

In the configuration in FIG. 3A, the light detectors 205, 208, and 210 correspond to a light receiver in claims. Further, the light detector 205 that receives forward scattered light corresponds to a first detector in claims. The light detector 210 that receives fluorescence corresponds to a second detector in claims.

Returning to FIG. 1, the particle sorting unit 30 includes bubble generators 31, 32. The bubble generators 31, 32 generate bubbles by heat. The particle sorting unit 30 adjusts, for each particle, a direction into which a particle flowing in the first flow path section 110 flows, by selecting the direction from a direction toward the second flow path section 120 and a direction toward the third flow path section 130.

Specifically, when the particle sorting unit 30 is driven, bubbles generated by the bubble generators 31, 32 are applied to a particle that flows in the first flow path section 110. Thus, the direction into which the particle positioned in the particle sorting unit 30 flows, is changed from the X-axis positive direction to the direction toward the third flow path section 130, and the particle flows toward the third flow path section 130. When the particle sorting unit 30 is not driven, the direction into which a particle positioned in the particle sorting unit 30 flows is not changed from the X-axis positive direction, and the particle flows toward the fifth flow path section 150 and flows into the second flow path section 120.

Whether the particle that has reached the position of the particle sorting unit 30 flows toward the third flow path section 130 or toward the second flow path section 120, is determined for each particle by a controller 13 on the basis of a result of detection by the particle detection unit 20. The particle of which the image is determined to be taken, is caused to flow toward the second flow path section 120, and the particle of which the image is determined to be not taken, is caused to flow toward the third flow path section 130. Such a determination will be described below with reference to FIG. 5A.

Thus, the particle sorting unit 30 causes a particle determined as an imaging target of the particle imaging unit 50 to flow straight without applying external force thereto, and guides the particle through the fifth flow path section 150 into the second flow path section 120. The particle sorting unit 30 changes a flow direction of a particle which is determined to be not an imaging target of the particle imaging unit 50, by applying external force thereto, and guides the particle into the third flow path section 130. Thus, only particles that are highly likely to be imaging targets can be stably guided into the second flow path section 120.

In the present embodiment, particles which are determined to be not imaging targets of the particle imaging unit 50 are caused to flow into the third flow path section 130 only. However, the particles may be caused to flow into the fourth flow path section 140 as well as the third flow path section 130. Further, the particle sorting unit 30 may include a piezoactuator having a piezoelectric body and electrodes, or an ultrasonic generator having a piezoelectric crystal substrate and comb-shaped electrodes, instead of the bubble generators 31, 32. In this case, a node of an ultrasonic standing wave generated by the piezoactuator or the ultrasonic generator is positioned on the Y-axis positive side or the Y-axis negative side relative to the central axis 112. Thus, the direction into which a particle positioned in the particle sorting unit 30 flows can be changed from the X-axis positive direction.

The third flow path section 130 and the fourth flow path section 140 branch from the first flow path section 110, between the first flow path section 110 and the second flow path section 120. Thus, a sheath liquid that flows in the first flow path section 110 is separated into the third flow path section 130, the fourth flow path section 140, and the fifth flow path section 150. The sheath liquid that flows in the third flow path section 130 and the sheath liquid that flows in the fourth flow path section 140 are stored in the not-illustrated waste liquid storing units. A particle that flows into the fifth flow path section 150 is caused to flow in the X-axis positive direction along the central axis 152 in the fifth flow path section 150, and flow into the second flow path section 120.

As described above, the third flow path section 130 and the fourth flow path section 140 are configured to be symmetric about the central axis 112 of the first flow path section 110. Thus, the sheath liquid that flows in the first flow path section 110 is caused to flow almost evenly into the third flow path section 130 and the fourth flow path section 140. Thus, a speed at which the particle flows through the fifth flow path section 150 into the second flow path section 120 is stabilized, and the particle imaging unit 50 is allowed to take a more accurate image.

The particle alignment unit 40 has piezoactuators 41, 42 disposed on the side surfaces of the second flow path section 120. The piezoactuators 41, 42 have piezoelectric bodies and electrodes. The piezoelectric body may be formed as a film or a bulk. A material of the piezoelectric body is, but is not limited to, $Pb(Zr, Ti)O_3$, $BaTiO_3$, $(K, Na)NbO_3$, $Pb(Mn, Nb)O_3$—$PbTiO_3$, $ZnO$, $SiO_2$, or the like. For vibration of the piezoelectric bodies, a vertical mode may be used, or a sliding mode may be used.

The particle alignment unit 40 aligns the positions of the particles with the central axis 122, and aligns, in the flow direction, the particles that flow in the second flow path section 120. The particle alignment unit 40 applies an ultrasonic wave to particles that flow in the second flow path section 120, from both sides of the second flow path section 120, in the direction perpendicular to the direction in which the particle imaging unit 50 takes an image and to the direction in which the particles flow, that is, in the Y-axis direction.

Specifically, as shown in FIG. 2F, when the particle alignment unit 40 is driven, ultrasonic standing waves are generated by the piezoactuators 41, 42. Nodes of the ultrasonic standing waves are positioned at the central axis 122 shown in FIG. 2B. Thus, the particles are caused to flow in the second flow path section 120 along the central axis 122, and the particles thus flow through an imaging region 51 on the downstream side. Therefore, the particle imaging unit 50 is allowed to take a more accurate image.

As a material of the member 121 of the second flow path section 120, a material that has a high rigidity and allows reduction of attenuation of a sonic wave is preferably used. Examples of a material having a high rigidity include quartz and silicon. When a material that allows reduction of attenuation of a sonic wave is used as a material of the member 121, acoustic force can be effectively applied to particles in the measurement sample. When a piezoactuator is used as the particle sorting unit 30, a material of the member 111 of the first flow path section 110 preferably also has a high rigidity and allows reduction of attenuation of a sonic wave, similarly to the member 121 of the second flow path section 120. Further, when an ultrasonic generator having a piezoelectric crystal substrate and comb-shaped electrodes is used as the particle sorting unit 30, a material that allows reduction of attenuation of a sonic wave is preferably used. Thus, acoustic force can be effectively applied to particles in the measurement sample. The third flow path section 130, the fourth flow path section 140, and the fifth flow path section 150 may be also formed from the same material as the second flow path section 120.

The particle alignment unit 40 may be any unit that can generate an ultrasonic standing wave, and may be an ultrasonic generator having a piezoelectric crystal substrate and comb-shaped electrodes, instead of the piezoactuators 41, 42. The configuration of the ultrasonic generator will be described with reference to Embodiment 7.

The particle imaging unit 50 applies light to the imaging region 51 in the second flow path section 120, receives light from the imaging region 51, and takes an image of a particle that flows in the imaging region 51. The imaging region 51 is the range in which an image is taken by the particle imaging unit 50. The size of the imaging region 51 is set so as to include a particle that flows along the central axis 122.

As shown in FIG. 3B, the particle imaging unit 50 includes a light source 501, a dichroic mirror 502, an object lens 503, and cameras 504, 505.

Light emitted from the light source 501 is laser light having a wavelength of about 488 nm. The dichroic mirror 502 causes the light emitted from the light source 501 to transmit therethrough, and reflects fluorescence. The light that transmits through the dichroic mirror 502 is condensed by the object lens 503. The condensed light is applied to the imaging region 51 shown in FIG. 1. Thus, when light is applied to a stained particle, fluorescence is generated from the particle. The fluorescence generated from the particle is condensed by the object lens 503. The dichroic mirror 502 reflects the fluorescence.

The cameras 504, 505 are TDI (Time Delay Integration) cameras. The camera 504 receives the fluorescences having different wavelengths, and outputs image information for each fluorescence. For example, the dichroic mirror 502 may have a plurality of reflection surfaces according to wavelengths of fluorescences, and a tilt angle of each reflection surface of the dichroic mirror 502 may be adjusted so as to separate into focusing areas in the camera 504 according to the wavelengths of the fluorescences, respectively. In this configuration, an image taken by the camera 504 is sectioned into a plurality of regions corresponding to the fluorescences, respectively. The image information for the regions is image information for the fluorescences, respectively. The camera 505 receives light that has transmitted through the particle, and outputs bright field image information.

The direction in which the cameras 504, 505 take images of the particle is the Z-axis direction. On the cross-section of the second flow path section 120, the width in the direction perpendicular to the imaging direction and to the particle flowing direction, that is, the width in the Y-axis direction is greater than the width in the imaging direction, that is, the width in the Z-axis direction. Therefore, the particles are less likely to overlap each other in the Z-axis direction, and the particle imaging unit 50 is thus allowed to take an image for each particle.

A flow rate of the sheath liquid and the measurement sample 12 in the second flow path section 120 is reduced from a flow rate of the sheath liquid and the measurement sample 12 in the first flow path section 110 due to the third flow path section 130 and the fourth flow path section 140. Specifically, the flow rate of the sheath liquid and the measurement sample 12 in the first flow path section 110 is 100 µL/s, whereas the flow rate of the sheath liquid and the measurement sample 12 in the second flow path section 120 is 30 µL/s. Therefore, the flow rate of the sheath liquid and the measurement sample 12 in the second flow path section 120 is less than or equal to ⅓ of the flow rate of the sheath liquid and the measurement sample 12 in the first flow path section 110. Further, the flow rate of the sheath liquid and the measurement sample 12 in each of the third flow path section 130 and the fourth flow path section 140 is 35 µL/s. Thus, a speed at which a particle flows in the second flow path section 120 is lower than a speed at which the particle flows in the first flow path section 110.

Further, the cross-sectional area of the second flow path section 120 is greater than the cross-sectional area of the first flow path section 110 as described above. Thus, a speed at which a particle flows in the second flow path section 120 is further reduced as compared to a speed at which the particle flows in the first flow path section 110. Specifically, a speed at which a particle flows in the first flow path section 110 is 1.0 m/s, whereas a speed at which the particle flows in the second flow path section 120 is 0.1 m/s. Therefore, the speed at which a particle flows in the second flow path section 120 is lower than or equal to ¹⁄₁₀ of the speed at which the particle flows in the first flow path section 110. Accordingly, even when a speed at which a particle flows in the first flow path section 110 is enhanced in order to extract an imaging target particle from a lot of particles, a speed at which the particle flows in the second flow path section 120 is greatly reduced, whereby the particle imaging unit 50 is allowed to take an accurate image of the particle. That is, an image of an imaging target particle can be taken with high quality while the processing speed of the particle imaging apparatus 10 is maintained.

The fifth flow path section 150 connects between the first flow path section 110 and the second flow path section 120, and the cross-sectional area of the fifth flow path section 150 is gradually increased toward the downstream side. Thus, a speed of a particle can be gradually reduced until the particle reaches the second flow path section 120 from the first flow path section 110. Therefore, the speed at which the particle flows in the second flow path section 120 is stabilized, and the particle imaging unit 50 is thus allowed to take an accurate image of the particle.

The cross-sectional area of each of the third flow path section 130 and the fourth flow path section 140 is gradually increased from the upstream side toward the downstream side. Thus, the measurement sample 12 flowing from the first flow path section 110 toward the third flow path section 130 or the fourth flow path section 140 is less likely to flow into the fifth flow path section 150. Therefore, the speed at which a particle flows in the second flow path section 120 is stabilized, and the particle imaging unit 50 is thus allowed to take an accurate image of the particle.

Returning to FIG. 1, a particle of which the image has been taken by the particle imaging unit 50, flows in the second flow path section 120, and is stored in the not-illustrated waste liquid storing unit. When the entirety of the measurement sample 12 has flowed through the flow path 100, the processing for the measurement sample 12 ends.

Figure 4:
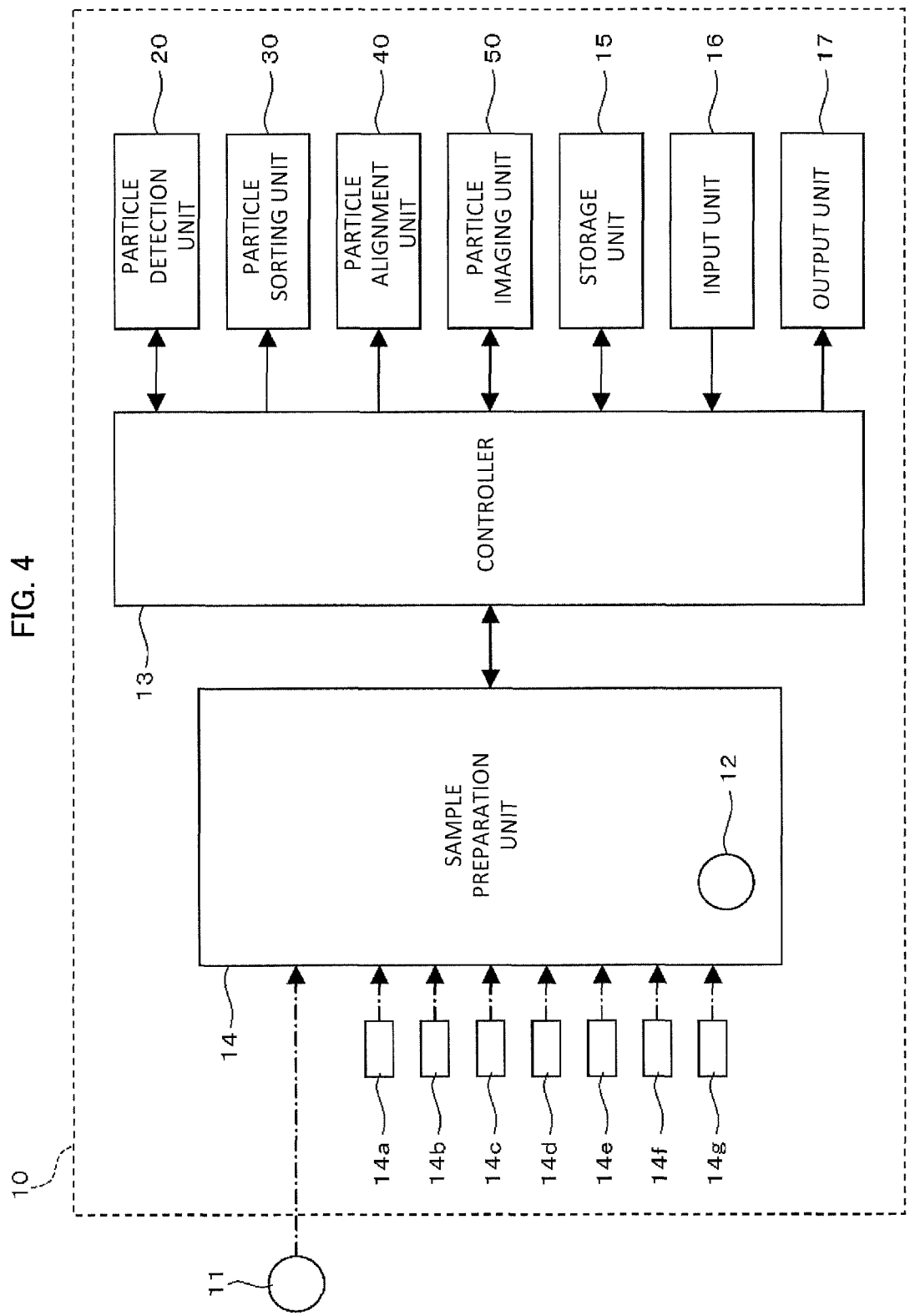
FIG. 4 is a block diagram illustrating a configuration of the particle imaging apparatus according to Embodiment 1.

As shown in FIG. 4, the particle imaging apparatus 10 includes the controller 13, a sample preparation unit 14, a storage unit 15, an input unit 16, and an output unit 17, in addition to the particle detection unit 20, the particle sorting unit 30, the particle alignment unit 40, and the particle imaging unit 50. The controller 13 includes a calculation processing circuit such as a CPU, and controls each component of the particle imaging apparatus 10 according to a program stored in the storage unit 15. The storage unit 15 includes a storage medium such as an ROM, an RAM, and a hard disk.

The sample preparation unit 14 receives the blood specimen 11 that is peripheral blood collected from a patient. To the sample preparation unit 14, containers that store reagents 14a to 14g are connected. The reagent 14a includes a hemolyzing agent for hemolyzing red blood cells. The reagent 14b includes a labeled CD45 antibody for detecting white blood cells. The reagent 14c includes a Ch17 probe which is to bind to chromosome 17. The reagent 14d includes a Her2 probe which is to bind to Her2 gene. The reagent 14e includes an antibody which is labelled with a dye named Alexa488 and which is to bind to a Ch17 probe. The reagent 14f includes an antibody which is labeled with a dye named PE and which is to bind to a Her2 probe. The reagent 14g includes a dye 7AAD for staining a nucleus. These dyes allow excitation for fluorescences having different wavelengths upon application of light that is emitted from the light source 501 and that has a wavelength of about 488 nm. The dye for the reagent 14e may be FITC instead of Alexa488. The dye for the reagent 14f may be PE-Cy7 instead of PE. The sample preparation unit 14 mixes the blood specimen 11 and the reagents 14a to 14g with each other to prepare the measurement sample 12. The measurement sample 12 is caused to flow in the flow path 100 shown in FIG. 1.

When excitation wavelengths for the dyes included in the reagents 14e, 14f, and 14g are different, the light source 501 is changed to a light source that emits a plurality of lights according to the excitation wavelengths for the dyes. As such a light source, a multi-light emitting laser having a plurality of light emitting elements mounted on a substrate can be used. Alternatively, the light source 501 may be configured to couple laser lights emitted from a plurality of semiconductor lasers by using a dichroic mirror. For example, examples of a dye that is different in an excitation wavelength from Alexa488 include Alexa647 and HOECHST. Alexa647 can be used in labeling for Her2 gene, and HOECHST can be used in labeling for a nucleus.

The controller 13 obtains signal waveforms corresponding to forward scattered light, side scattered light, and fluorescence on the basis of signals outputted by the light detectors 205, 208, and 210 of the particle detection unit 20. The controller 13 obtains a peak value of the signal waveform corresponding to each light for each particle. The peak value of the signal waveform of a forward scattered light signal, the peak value of the signal waveform of a side scattered light signal, and the peak value of the signal waveform of the fluorescence correspond to the intensity of the forward scattered light signal, the intensity of the side scattered light signal, and the intensity of the fluorescence signal.

The controller 13 stores in the storage unit 15 the peak values of the signal waveforms which correspond to the lights, respectively, obtained for each particle. The controller 13 drives the particle sorting unit 30 so as to select a direction into which the particle flows. The controller 13 drives the particle alignment unit 40 so as to align the positions of the particles that flow in the second flow path section 120, with the central axis 122. The controller 13 generates an image of the particle on the basis of the output signals from the cameras 504, 505 of the particle imaging unit 50, and stores the generated image in the storage unit 15. The controller 13 analyzes the taken image and displays the image of the particle on the output unit 17. The controller 13 receives an instruction from an operator through the input unit 16, and causes the output unit 17 to display the taken image of the particle and the like. The input unit 16 is a mouse and/or a keyboard, and the output unit 17 is a display such as a liquid crystal panel.

Next, a process performed by the particle imaging apparatus 10 will be described with reference to flow charts. When an operator makes an instruction for start, the controller 13 drives the particle imaging apparatus 10, to aspirate the blood specimen 11 and supply the blood specimen 11 to the sample preparation unit 14, and causes the processes shown in FIGS. 5A-5C to be stated and performed in parallel.

Figure 5C:
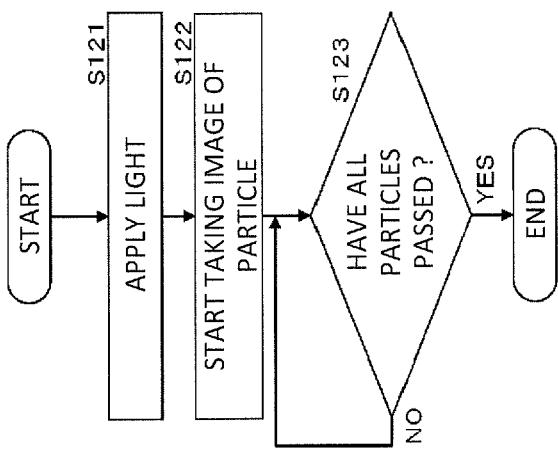
FIG. 5A to FIG. 5C are flow charts showing a process performed by the particle imaging apparatus according to Embodiment 1.
Figure 5B:
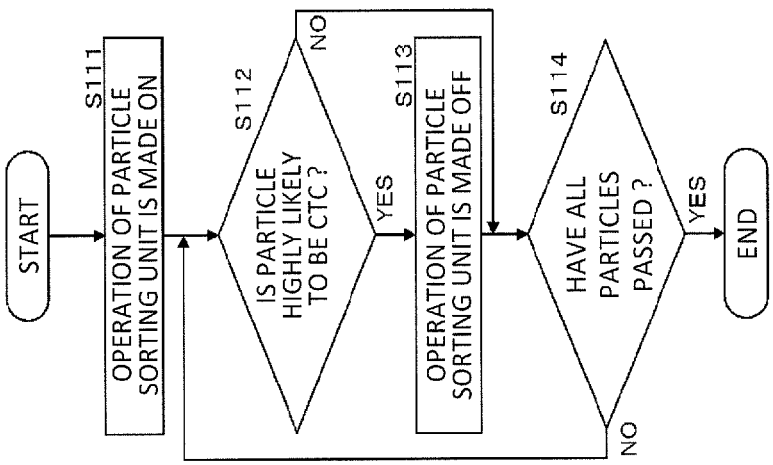
Figure 5A:
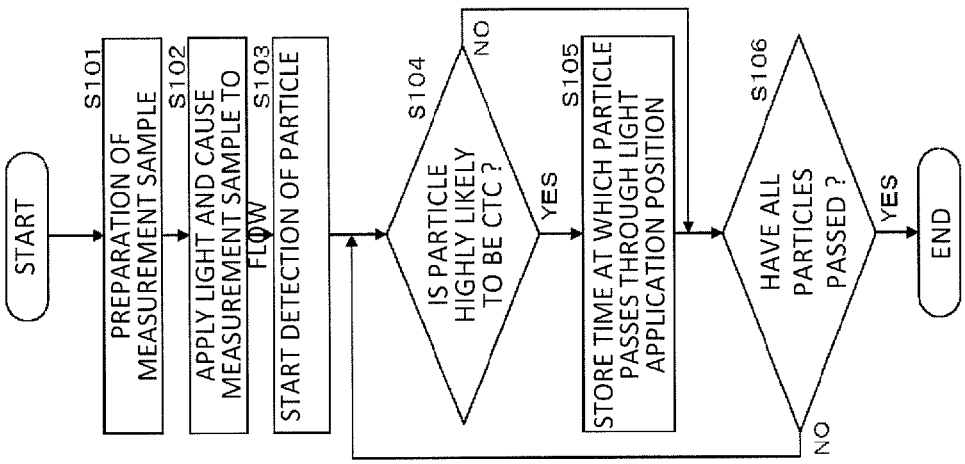

As shown in FIG. 5A, in step S101, the sample preparation unit 14 mixes the blood specimen 11 and the reagents 14a to 14g with each other to prepare the measurement sample 12. When the measurement sample 12 is prepared, red blood cells in the blood specimen 11 are hemolyzed by the action of the reagent 14a, and the labeled CD45 antibody in the reagent 14b and the surface antigen CD45 of a white blood cell in the blood specimen 11 bind to each other. Further, when the measurement sample 12 is prepared, the blood specimen 11 and the reagents 14c to 14g are mixed with each other.

In step S102, the controller 13 drives the light source 201 of the particle detection unit 20, to apply light to the light application position 21 in the first flow path section 110, and causes the measurement sample 12 to flow from the upstream side of the first flow path section 110 at a predetermined speed. In step S103, the controller 13 causes the light detectors 205, 208, and 210 of the particle detection unit 20 to detect a forward scattered light signal, a side scattered light signal, and a fluorescence signal, respectively, and starts detection of a particle in the measurement sample 12 that flows in the first flow path section 110. The fluorescence signal from the labeled CD45 antibody is obtained by the light detector 210. The controller 13 obtains the intensity of the forward scattered light signal, the intensity of the side scattered light signal, and the intensity of the fluorescence signal, for each particle.

In step S104, the controller 13 determines whether or not a particle at the light application position 21 is highly likely to be a CTC. Specifically, when the intensity of the fluorescence signal is lower than or equal to a predetermined threshold value, and the intensity of the forward scattered light signal is higher than or equal to a predetermined threshold value, the controller 13 determines that the particle at the light application position 21 is highly likely to be a CTC. That is, when, in a particle, the fluorescence signal has a value greater than the predetermined threshold value and the forward scattered light signal has an intensity lower than the predetermined threshold value, the particle is excluded from imaging targets. When the particle is a CTC, since the particle dose not bind to the labeled CD45 antibody, the intensity of the fluorescence signal is lower than or equal to the predetermined value. Further, when the particle is a CTC, since the size of the particle is large, the intensity of the forward scattered light signal is higher than or equal to the predetermined threshold value. Thus, in step S104, when the particle is other than white blood cells and the size of the particle is large, the controller 13 determines that the particle is highly likely to be a CTC.

When the sample is prepared, the reagent 14a for hemolyzing red blood cells may not be used. Also in this case, since red blood cells have small sizes and the intensity of the forward scattered light signal is lower than the predetermined threshold value, the red blood cells in the measurement sample 12 are excluded from the imaging targets.

When the determination in step S104 is YES, the controller 13 stores, in step S105, a time at which the particle determined in step S104 to be highly likely to be a CTC passes through the light application position 21. In step S106, the controller 13 determines whether or not the measurement sample 12 has flowed through the first flow path section 110, and all the particles have passed through the light application position 21. The controller 13 repeats the process steps of steps S104 and S105 for each of the particles positioned at the light application position 21 until all the particles have passed through the light application position 21. When all the particles have passed through the light application position 21, the process is ended.

As shown in FIG. 5B, in step S111, the controller 13 causes the operation of the particle sorting unit 30 to be ON. In step S112, the controller 13 determines whether or not the particle positioned in the particle sorting unit 30 is highly likely to be a CTC. Specifically, in a case where a predetermined time period has elapsed since the time stored in step S105, the controller 13 determines that the particle determined to be highly likely to be a CTC in step S104 in FIG. 5A is positioned in the particle sorting unit 30.

When the determination in step S112 is YES, the controller 13 causes the operation of the particle sorting unit 30 to be OFF in step S113. Thus, the particle determined to be highly likely to be a CTC is caused to flow though the fifth flow path section 150 into the second flow path section 120. Meanwhile, when the determination in step S112 is NO, the controller 13 continues to make the operation of the particle sorting unit 30 ON. Therefore, the particle determined to be less likely to be a CTC is caused to flow into the third flow path section 130. Thus, the controller 13 drives the particle sorting unit 30 on the basis of the intensity of the fluorescence signal, thereby adjusting a direction into which the particle flowing in the first flow path section 110 flows.

In step S114, the controller 13 determines whether or not the measurement sample 12 has flowed through the first flow path section 110, and all the particles have passed through the particle sorting unit 30. The controller 13 repeats the process steps of steps S112 and S113 for each of the particles positioned in the particle sorting unit 30 until all the particles have passed through the particle sorting unit 30. When all the particles have passed through the particle sorting unit 30, the process is ended.

As shown in FIG. 5C, in step S121, the controller 13 drives the light source 501 of the particle imaging unit 50, to apply light to the imaging region 51 in the second flow path section 120. In step S122, the controller 13 drives the cameras 504, 505 of the particle imaging unit 50 to start taking images of a particle. Thus, the controller 13 drives the particle imaging unit 50, thereby to take images of the particle that is highly likely to be a CTC. The controller 13 monitors images taken by the cameras 504, 505, extracts taken images including a particle, from a series of taken images, as images of the particle, and stores the images in the storage unit 15.

In step S123, the controller 13 determines whether or not the measurement sample 12 has flowed through the first flow path section 110, and all the particles have passed through the particle imaging unit 50. The controller 13 causes images of the particles that pass through the imaging region 51 to be continuously taken until all the particles have passed through the particle imaging unit 50. When all the particles have passed through the imaging region 51, the process is ended.

When the processes of FIGS. 5A-5C have been ended, an operator inputs an instruction for displaying a result, through the input unit 16, to the particle imaging apparatus 10.

Figure 6B:
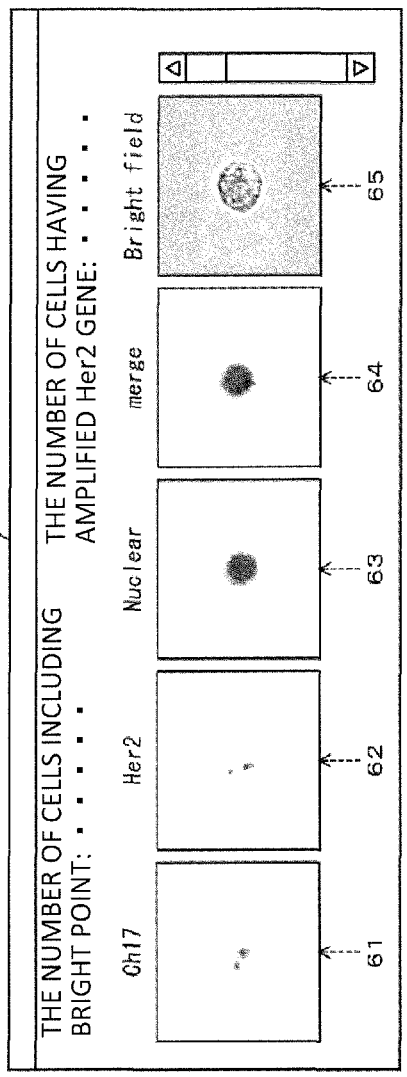
FIGS. 6B and 6C illustrate screens displayed on an output unit according to Embodiment 1.
Figure 6C:
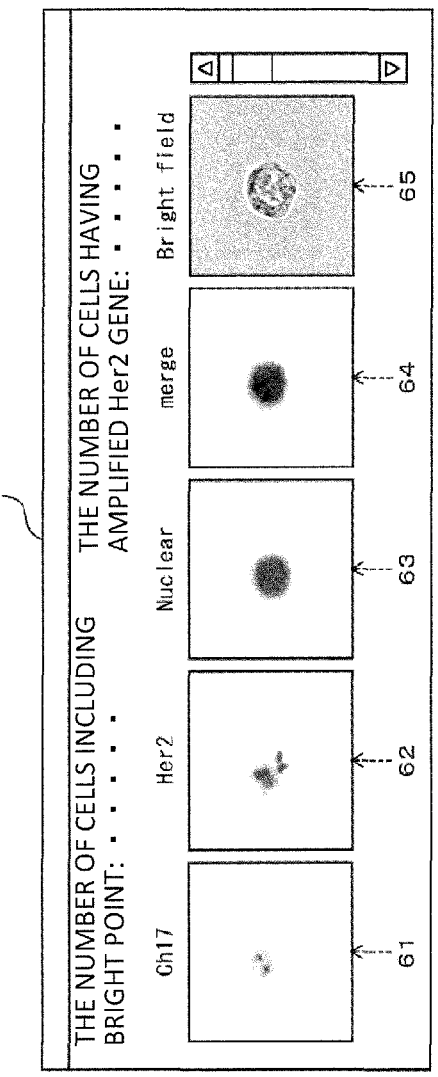
Figure 6A:
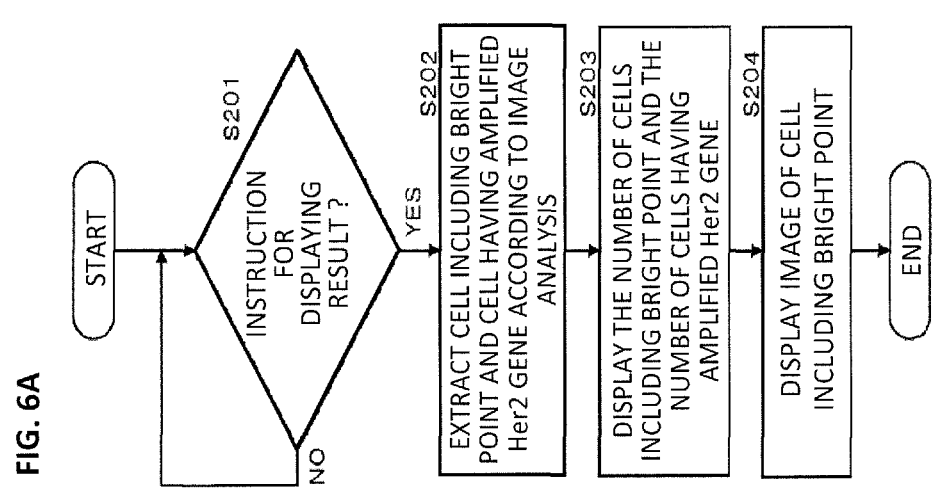
FIG. 6A is a flow chart showing a display process performed by the particle imaging apparatus according to Embodiment 1.

As shown in FIG. 6A, in step S201, the controller 13 determines whether or not an instruction for displaying a result has been inputted by the operator. When the determination in step S201 is YES, the controller 13 analyzes, in step S202, images of all the particles taken in the process shown in FIG. 5C, and extracts cells each including, in the nucleus, a bright point based on chromosome 17 and a bright point based on Her2 gene. Further, in step S202, the controller 13 analyzes the images of the extracted cells, determines, for each cell, whether or not the Her2 gene has been amplified, and extracts, as a CTC, a cell having the amplified Her2 gene. As a cell having the amplified Her2 gene, that is, as a CTC, the controller 13 extracts a cell including, in the nucleus, three or more bright points based on the Her2 gene. In step S203, the controller 13 causes the output unit 17 to display the number of cells including the bright points and the number of cells (CTCs) having the amplified Her2 gene, on the basis of the result of extraction in step S202. In step S204, the controller 13 causes the output unit 17 to display the images of the cells which include the bright points and which have been extracted in step S202.

As shown in FIGS. 6B and 6C, in steps S203 and S204, a screen 60 is displayed on the output unit 17. On the screen 60, the number of cells including the bright points, the number of cells (CTCs) having the amplified Her2 gene, and images of the cell including the bright points are displayed. The operator is allowed to know whether or not the Her2 gene has been amplified with reference to the number of the cells. Therefore, useful information that allows a doctor and the like to determine an optimal therapeutic drug, can be provided.

Five images that are laterally aligned are for the same particle. The five images are an image 61 of fluorescence generated by a dye for labeling for a gene in chromosome 17, an image 62 of fluorescence generated by a dye for labeling for Her2 gene, an image 63 of fluorescence generated by a dye for staining the nucleus, an image 64 obtained by the images 61 to 63 being merged, and a bright field image 65 in order, respectively, from the left side. The images 61 to 64 are obtained by reversing the gradation and then performing conversion to gray scale images.

The images of the particle shown in FIG. 6B are images representing a cell in which the Her2 gene is not amplified. The images of the particle shown in FIG. 6C are images of a breast cancer cell having the amplified Her2 gene. In a case where the number of images of the particle including bright points is plural, an operator is allowed to switch between the images of the particle on the screen 60 and perform display thereon. Further, a button or the like that allows an image of a cell having the amplified Her2 gene, and an image of a cell in which the Her2 gene is not amplified to be individually displayed, may be separately provided on the screen 60.

The number of the bright points in the image 61 represents the number of genes (Ch17) in chromosome 17. The number of the bright points in the image 62 represents the number of the Her2 genes. The bright point in the image 63 represents the nucleus. Thus, the operator can know whether or not the genes in chromosome 17 and Her2 genes are in the nucleus, by actually referring to the images. Further, when the Her2 gene is not amplified, the number of the bright points in each of the images 61 and 62 is two as shown in FIG. 6B. When the Her2 gene has been amplified, the number of the bright points in the image 61 is two, and the number of the bright points in the image 62 is greater than two, as shown in FIG. 6C. Thus, the operator can know whether or not the Her2 gene has been amplified by actually referring to the images.

<Embodiment 2>

In Embodiment 1, the third flow path section 130 and the fourth flow path section 140 are configured so as to increase the cross-sectional areas toward the downstream side. However, as shown in FIG. 7A, the cross-sectional area thereof may be constant. In Embodiment 2, only the shape of the third flow path section 130 and the shape of the fourth flow path section 140 are different from those in Embodiment 1 as shown in FIG. 7A. The other configuration and the process of the particle imaging apparatus 10 are the same as those in Embodiment 1.

Also in Embodiment 2, a flow rate of the measurement sample 12 in the second flow path section 120 is reduced from a flow rate of the measurement sample 12 in the first flow path section 110. Thus, a speed at which a particle flows in the second flow path section 120 is lower than a speed at which the particle flows in the first flow path section 110. Therefore, the particle imaging unit 50 is allowed to take an accurate image of the particle.

<Embodiment 3>

In Embodiment 2, an end portion of the first flow path section 110 on the downstream side is divided into three portions, and the three portions are connected to the third flow path section 130, the fourth flow path section 140, and the fifth flow path section 150, respectively. However, as shown in FIG. 7B, the third flow path section 130 and the fourth flow path section 140 may branch from the side surface of the first flow path section 110. In Embodiment 3, only a position at which the third flow path section 130 branches and a position at which the fourth flow path section 140 branches are different from those in Embodiment 2. The other configuration and the process of the particle imaging apparatus 10 are the same as those in Embodiment 2.

In Embodiment 3, since the cross-sectional area is increased at the end portion of the first flow path section 110 on the downstream side, the flow speed is temporarily reduced. However, the flow speed is increased again at the end portion of the fifth flow path section 150 on the upstream side. When the flow speed is thus changed non-linearly, a speed at which a particle flows in the second flow path section 120 becomes unstable. Therefore, according to comparison between Embodiments 2 and 3, the third flow path section 130 and the fourth flow path section 140 preferably branch from the first flow path section 110 as in Embodiment 2.

<Embodiment 4>

As shown in FIG. 7C, the cross-sectional area of the fifth flow path section 150 may be constant near the end portion on the upstream side in Embodiment 3. In Embodiment 4, the shape of the fifth flow path section 150 is different from that in Embodiment 3, and the cross-sectional areas of the third flow path section 130 and the fourth flow path section 140 are greater than those in Embodiment 3. The other configuration and the process of the particle imaging apparatus 10 are the same as those in Embodiment 3.

<Embodiment 5>

As shown in FIG. 8A, the fourth flow path section 140 may be omitted in Embodiment 4. Embodiment 5 is different from Embodiment 4 in that, in Embodiment 5, the fourth flow path section 140 is omitted. The other configuration and the process of the particle imaging apparatus 10 are the same as those in Embodiment 4.

<Embodiment 6>

As shown in FIG. 8B, the fifth flow path section 150 and the second flow path section 120 may be tilted in Embodiment 5. Embodiment 6 is different from Embodiment 5 in that, in Embodiment 6, the fifth flow path section 150 and the second flow path section 120 are tilted. Further, as shown in FIG. 8C, in Embodiment 6, in the process shown in FIG. 5B, step S113 is omitted and steps S301 and S302 are added. The other configuration and the other process of the particle imaging apparatus 10 are the same as those in Embodiment 5.

As shown in FIG. 8C, when it is determined that a particle positioned in the particle sorting unit 30 is highly likely to be a CTC, the controller 13 drives the bubble generators 31, 32 of the particle sorting unit 30 so as to cause the particle to flow downward in step S301. Meanwhile, when it is determined that a particle positioned in the particle sorting unit 30 is not highly likely to be a CTC, the controller 13 drives the bubble generators 31, 32 of the particle sorting unit 30 so as to cause the particle to flow upward in step S302.

<Embodiment 7>

As shown in FIG. 9, the flow path 100 may be provided on a piezoelectric crystal substrate 101 having a transmitting property in Embodiment 4.

Figure 10A:
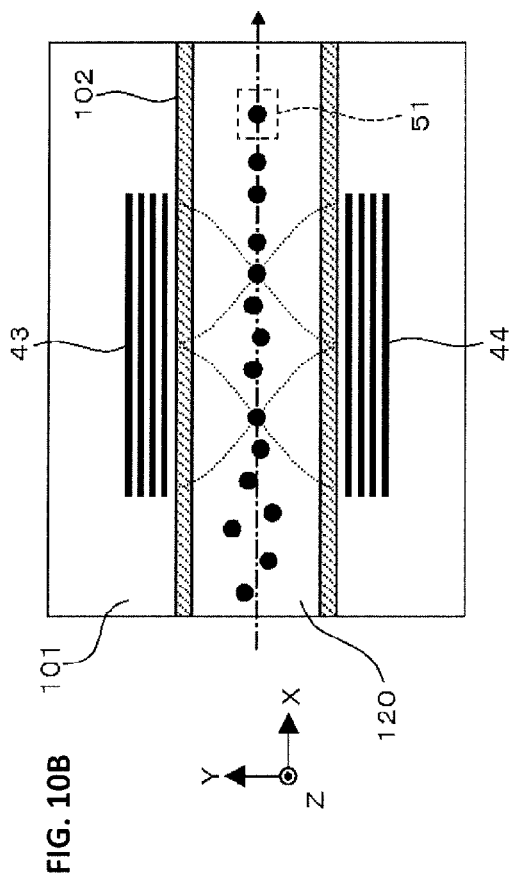
FIG. 10A is a schematic diagram illustrating formation of a flow path by a member adhered onto a piezoelectric crystal substrate according to Embodiment 7.

The piezoelectric crystal substrate 101 is formed from $LiNbO_3$. A member 102 formed from PDMS is adhered onto the piezoelectric crystal substrate 101. Each flow path section of the flow path 100 is formed as shown in, for example, FIG. 10A by the member 102 formed from PDMS being adhered onto the piezoelectric crystal substrate 101. The first flow path section 110, the second flow path section 120, and the fifth flow path section 150 have the cross-sectional shapes as shown in FIGS. 2A, 2B and 2E, respectively. The third flow path section 130 and the fourth flow path section 140 have rectangular cross-sectional shapes.

The flow path 100 further includes a sixth flow path section 161, a seventh flow path section 162, and an eighth flow path section 163 on the side upstream of the first flow path section 110. The seventh flow path section 162 and the eighth flow path section 163 merge into the sixth flow path section 161 from the Y-axis positive side and the Y-axis negative side of the sixth flow path section 161. These flow path sections are each formed also by the member 102 being adhered onto the piezoelectric crystal substrate 101, and these flow path sections also have rectangular cross-sectional shapes. The measurement sample 12 flows from the upstream side of the sixth flow path section 161. Particles included in the measurement sample 12 flow in the first flow path section 110 in a state where the particles are surrounded by a sheath liquid that flows from the upstream side of each of the seventh flow path section 162 and the eighth flow path section 163.

The components of the particle imaging apparatus 10 except for the flow path 100 are the same as those in Embodiment 1. Hereinafter, difference from Embodiment 1 will be described.

Figure 10B:
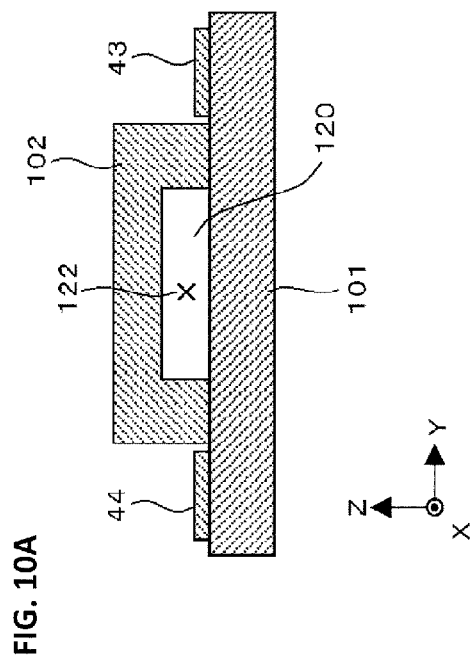
FIG. 10B is a schematic diagram illustrating forming of ultrasonic standing wave according to Embodiment 7.
Figure 10C:
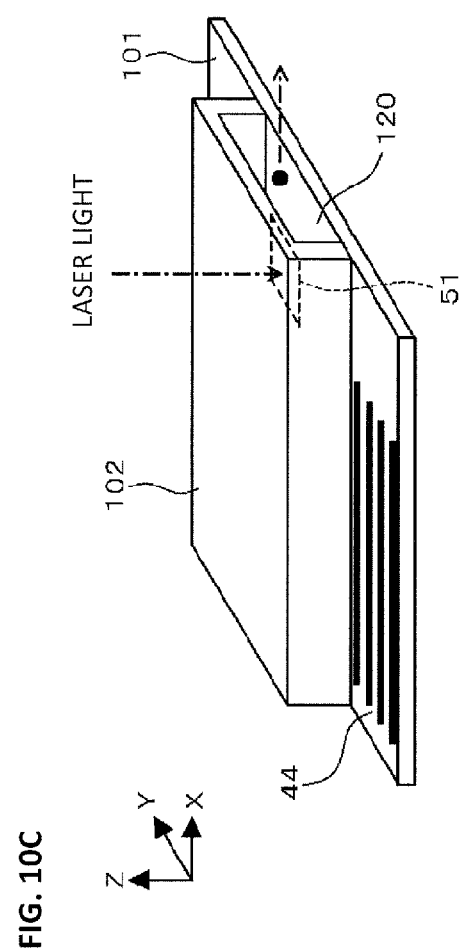
FIG. 10C is a perspective view schematically illustrating the piezoelectric crystal substrate, the member, and a comb-shaped electrode according to Embodiment 7.

As shown in FIGS. 10B and 10C, the particle alignment unit 40 includes the comb-shaped electrodes 43, 44 formed on the surface of the piezoelectric crystal substrate 101 by a semiconductor manufacturing technique. The particle alignment unit 40 causes electric current to flow through the comb-shaped electrodes 43, 44, thereby applying an ultrasonic wave to a particle that flows in the second flow path section 120. When electric current flows through the comb-shaped electrodes 43, 44, the piezoelectric crystal substrate 101 near the comb-shaped electrodes 43, 44 vibrates, and an ultrasonic standing wave is generated. That is, the comb-shaped electrodes 43, 44 and the piezoelectric crystal substrate 101 near the comb-shaped electrodes 43, 44 function as an ultrasonic generator in conjunction with each other. Nodes of the ultrasonic standing waves are positioned at the central axis 122 shown in FIG. 10A. Thus, a particle flows in the second flow path section 120 along the central axis 122, whereby the particle passes through the imaging region 51 on the downstream side. Therefore, the particle imaging unit 50 on the downstream side is allowed to assuredly take an image of the particle.

As shown in FIG. 9, the particle sorting unit 30 includes, instead of the bubble generators 31, 32, comb-shaped electrodes 33, 34 formed on the surface of the piezoelectric crystal substrate 101 by a semiconductor manufacturing technique. Also in this case, the comb-shaped electrodes 33, 34 and the piezoelectric crystal substrate 101 near the comb-shaped electrodes 33, 34 function as an ultrasonic generator in conjunction with each other. When electric current flows through the comb-shaped electrodes 33, 34, the piezoelectric crystal substrate 101 near the comb-shaped electrodes 33, 34 vibrates, and an ultrasonic standing wave is generated. Nodes of the ultrasonic standing waves are positioned on the Y-axis positive side relative to the central axis 112. Thus, a particle is caused to flow into the third flow path section 130.

Near the upstream side of the first flow path section 110, a particle alignment unit 70 similar to the particle alignment unit 40 is mounted. The particle alignment unit 70 includes comb-shaped electrodes 71, 72. Thus, a particle flows in the first flow path section 110 along the central axis 112 of the first flow path section 110.

Figure 11A:
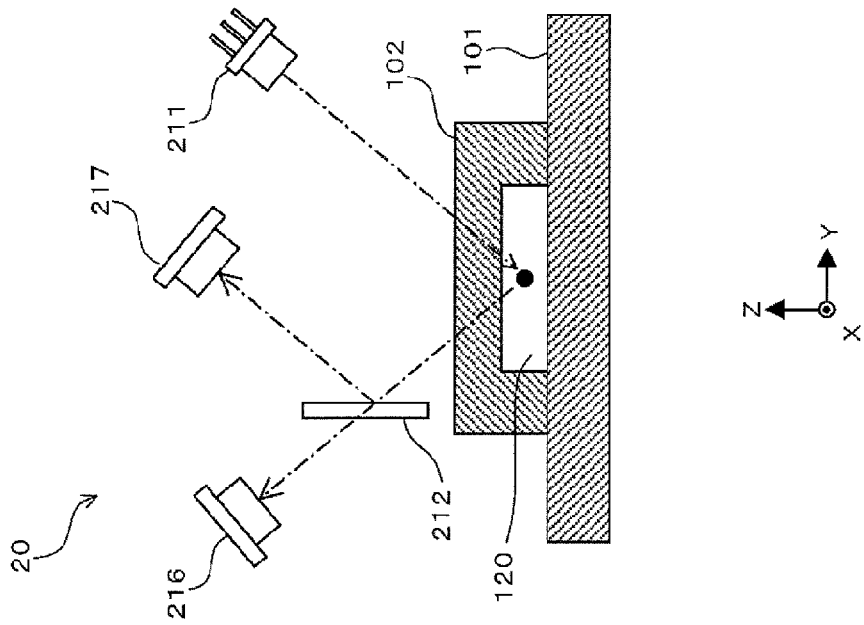
FIG. 11A is a schematic diagram illustrating a particle detection unit according to Embodiment 7 as viewed in the X-axis negative direction.

As shown in FIG. 11A, the particle detection unit 20 includes a light source 211, a dichroic mirror 212, condenser lenses 213, 215, and light detectors 214, 216, 217. The light source 211 is similar to the light source 201 in FIG. 2A. The light detectors 214, 216, 217 are similar to the light detectors 205, 208, 210, respectively, in FIG. 2A. Light emitted from the light source 211 passes through the dichroic mirror 212 and is applied to a particle. Thus, forward scattered light, side scattered light, and fluorescence are generated. The forward scattered light and the side scattered light are condensed by the condenser lenses 213 and 215, respectively. The fluorescence is reflected by the dichroic mirror 212. The light detectors 214, 216, 217 receive the forward scattered light, the side scattered light, and the fluorescence, respectively.

Figure 11B:
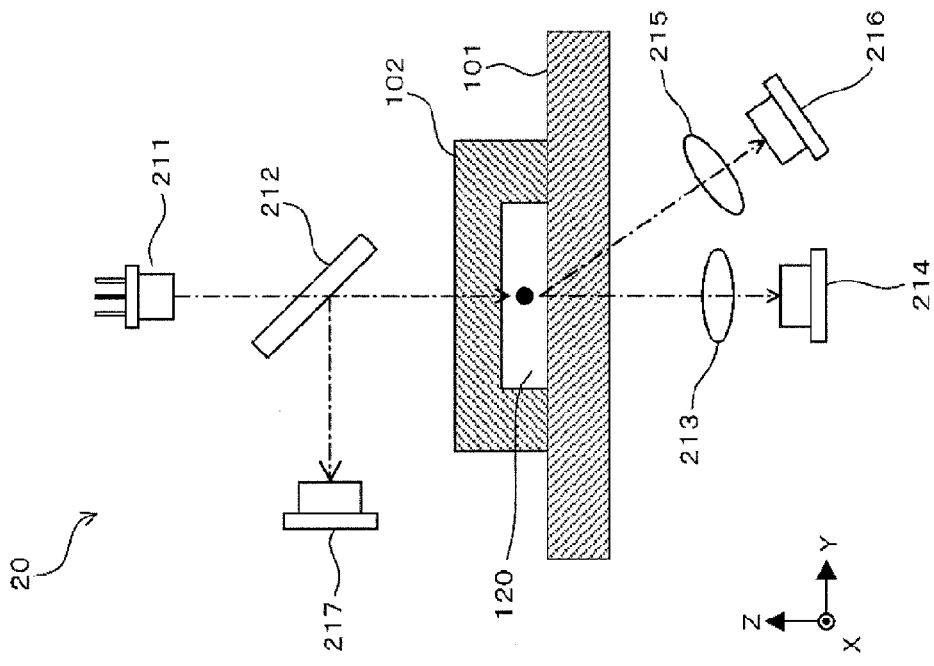
FIG. 11B is a schematic diagram illustrating a modification of the particle detection unit according to Embodiment 7.

In a case where the piezoelectric crystal substrate 101 does not have a transmitting property, the particle detection unit 20 has a configuration shown in FIG. 11B instead of the configuration shown in FIG. 11A. In FIG. 11B, light emitted from the light source 211 is applied diagonally to a particle. The light detector 216 receives side scattered light that has been transmitted through the dichroic mirror 212, and the light detector 217 receives fluorescence reflected by the dichroic mirror 212. In this case, forward scattered light cannot be received. Therefore, the configuration shown in FIG. 11B can be used only when the intensity of forward scattered light is not used in the following process.

<Embodiment 8>

As shown in FIG. 12A, Embodiment 8 is different from Embodiment 1 in that, in Embodiment 8, the particle sorting unit 30 includes a laser light source 35 that emits high-output laser light, instead of the bubble generators 31, 32. Further, the third flow path section 130 and the fourth flow path section 140 are omitted and the width of the second flow path section 120 in the Y-axis direction is increased. Moreover, in Embodiment 8, as shown in FIG. 12B, step S113 is omitted and step S311 is added in the process shown in FIG. 5B. The other configuration and the other process of the particle imaging apparatus 10 are the same as those in Embodiment 1.

As shown in FIG. 12B, when it is determined that a particle positioned in the particle sorting unit 30 is not a particle that is highly likely to be a CTC, the controller 13 causes laser light to be applied to the first flow path section 110 to break the particle positioned in the particle sorting unit 30 in step S311. That is, the controller 13 causes particles other than imaging target particles to be broken.

Also in Embodiment 8, only imaging target particles are caused to flow into the second flow path section 120. Further, the cross-sectional area of the second flow path section 120 is greater than the cross-sectional area of the first flow path section 110. Therefore, a speed at which a particle flows in the second flow path section 120 is lower than a speed at which the particle flows in the first flow path section 110. Therefore, images of the imaging target particles can be taken with high quality while the processing speed of the particle imaging apparatus 10 is maintained.

<Embodiment 9>

Figure 13A:
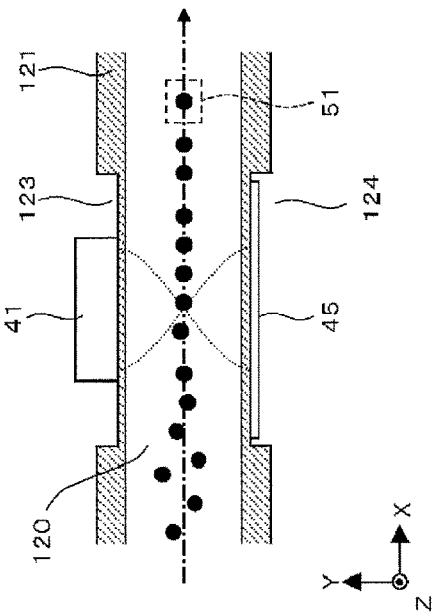
FIGS. 13A and 13B are schematic diagrams illustrating cross-sections of a second flow path section according to Embodiment 9.
Figure 13C:
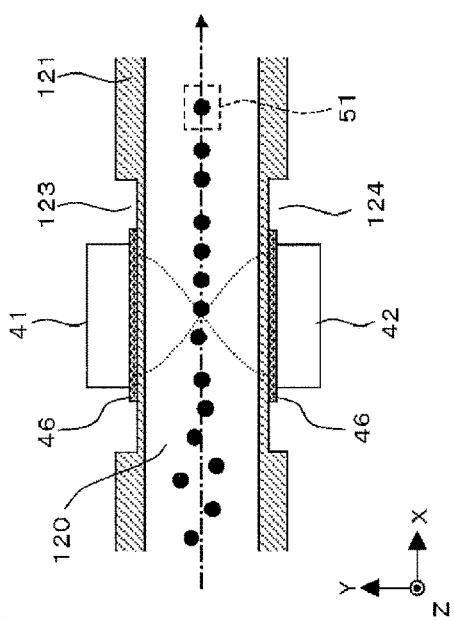
FIGS. 13C and 13D are schematic diagrams each illustrating an example of a configuration obtained by the configuration according to Embodiment 9 being partially modified.
Figure 13B:
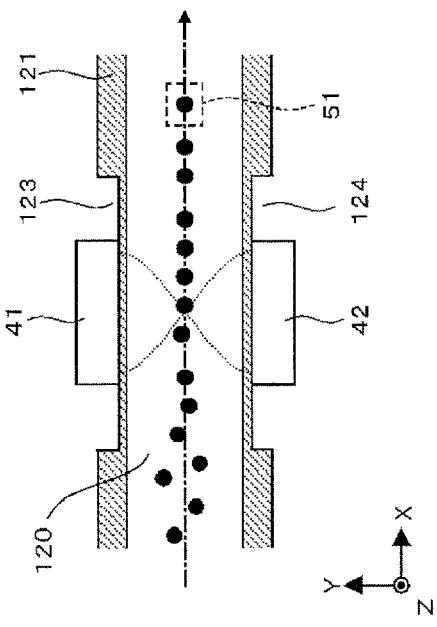

As shown in FIGS. 13A and 13B, in Embodiment 9, the thickness of the member 121 of the second flow path section 120 is different from that in Embodiment 1. The member 121 has rectangular recesses 123, 124 in side surface portions in which the piezoactuators 41, 42 are disposed. By the recesses 123, 124, in the member 121, the thickness of the side surface portions in which the piezoactuators 41, 42 are disposed is less than those of the other portions.

Thus, since the recesses 123, 124 are formed in the member 121 and the thickness of the member 121 is reduced, ultrasonic waves generated by the piezoactuators 41, 42 can be inhibited from being attenuated when the ultrasonic waves propagate through the member 121. Therefore, an ultrasonic standing wave can be generated in the second flow path section 120 with high precision. Thus, particles can be aligned near the central axis 122 with enhanced precision.

As shown in FIG. 13C, instead of the piezoactuator 42, a reflector plate 45 that reflects acoustic wave may be mounted in the recess 124. In this configuration, an ultrasonic standing wave is generated in the second flow path section 120 by: an ultrasonic wave applied to the second flow path section 120 by the piezoactuator 42; and a reflection wave obtained by the ultrasonic wave being reflected by the reflector plate 45. By adjusting the width of the second flow path section 120 in the Y-axis direction, or an amplitude and a frequency of an ultrasonic wave applied to the second flow path section 120 by the piezoactuator 42, an ultrasonic standing wave can be generated in the second flow path section 120. In the configuration in FIG. 13C, the piezoactuator 42 can be omitted, whereby the configuration can be simplified and cost can be reduced.

Also in the configuration shown in FIG. 2F in Embodiment 1, instead of the piezoactuator 42, the reflector plate 45 that reflects acoustic wave may be similarly mounted. One of the two piezoactuators 41, 42 that sandwich the second flow path section 120 in the Y-axis direction may be replaced with the reflector plate 45.

In the configuration in FIG. 13C, in a case where an acoustic impedance of the member 121 is higher than an acoustic impedance of a sheath liquid and the measurement sample 12 that flow in the second flow path section 120, an ultrasonic wave outputted into the second flow path section 120 by the piezoactuator 41 is reflected by the inner side surface of the second flow path section 120 on the Y-axis negative side. Therefore, in a case where an acoustic impedance of the member 121 is higher than an acoustic impedance of a sheath liquid and the measurement sample 12 that flow in the second flow path section 120, the reflector plate 45 can be omitted. Also in the configuration in FIG. 2F, in a case where an acoustic impedance of the member 121 is higher than an acoustic impedance of a sheath liquid and the measurement sample 12 that flow in the second flow path section 120, one of the piezoactuators 41, 42 can be similarly omitted.

In order to widen a sound field, a plurality of the piezoactuators 41 may be disposed in the X-axis direction. In a case where the reflector plate 45 is disposed so as to oppose the piezoactuator 41, a plurality of sets each including the piezoactuator 41 and the reflector plate 45 may be disposed in the X-axis direction. Also in a case where the piezoactuators 41, 42 are disposed so as to oppose each other, a plurality of sets each including the piezoactuators 41, 42 may be disposed in the X-axis direction. Such a configuration can be used similarly in the configuration in FIG. 2F.

Figure 13D:
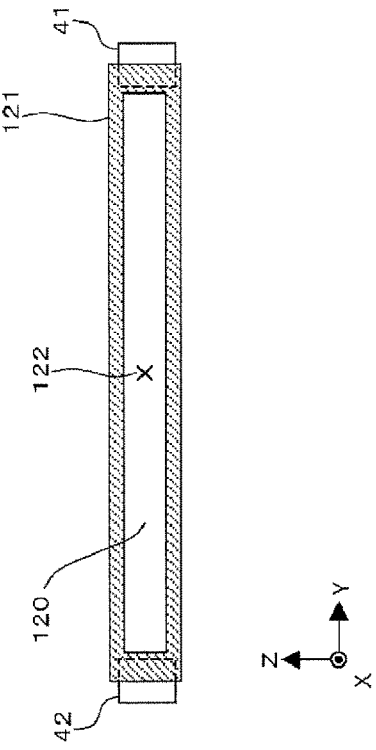

As shown in FIG. 13D, the piezoactuators 41, 42 may be mounted so as to be each pressed against the side surface of the member 121 of the second flow path section 120 through an acoustic coupling agent 46. Preferably, an acoustic impedance of the acoustic coupling agent 46 is approximately equal to an acoustic impedance of the member 121 of the second flow path section 120.

In the configuration in FIG. 13D, an acoustic coupling property of the piezoactuators 41, 42 is enhanced with respect to the second flow path section 120, whereby ultrasonic waves generated by the piezoactuators 41, 42 can more easily propagate through the second flow path section 120. Therefore, an ultrasonic standing wave can be generated in the second flow path section 120 with high precision. Thus, particles can be aligned near the central axis 122 with enhanced precision.

Also in the configuration shown in FIG. 2F in Embodiment 1, the acoustic coupling agents 46 may be similarly disposed between the piezoactuators 41, 42 and the side surfaces of the member 121. Further, in the configuration in FIG. 13C, the acoustic coupling agent 46 may be disposed between the reflector plate 45 and the side surface of the member 121 as well as between the piezoactuator 41 and the side surface of the member 121. In a case where the acoustic coupling agent 46 is not used, the piezoactuators 41, 42 and the reflector plate 45 are preferably brought into close contact with the side surfaces of the member 121 of the second flow path section 120 in order to enhance propagation of the ultrasonic wave.

In the member 121 of the second flow path section 120, portions in which the piezoactuators 41, 42 are disposed may not necessarily have the same thickness. In the member 121, when the portions in which the piezoactuators 41, 42 are disposed have thicknesses different from each other, sonic waves outputted from the piezoactuators 41, 42 propagate through the member 121 at different speeds. Thus, a position of a node of the ultrasonic standing wave generated in the second flow path section 120 can be shifted from the central axis 122 in the Y-axis direction. In this method, positions at which particles are aligned can be controlled. In a case where, as in the configuration in FIG. 13D, the acoustic coupling agents 46 are used, a thickness and an acoustic impedance of each acoustic coupling agent 46 may be adjusted for the same purpose, or one of the acoustic coupling agents 46 may be omitted.

<Embodiment 10>

Figure 14A:
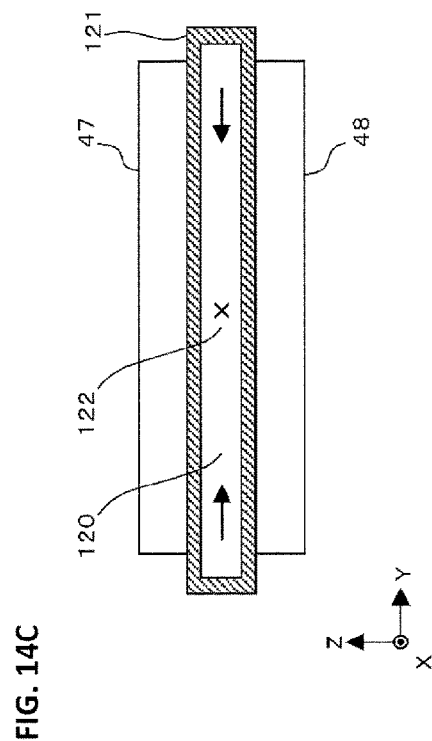
FIG. 14A is a schematic diagram illustrating a cross-section of a second flow path section according to Embodiment 10.
Figure 14C:
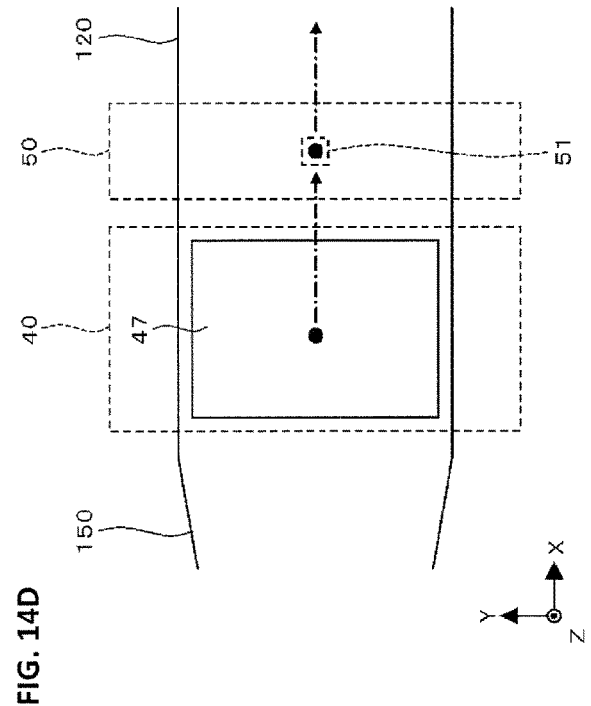
FIG. 14C is a schematic diagram illustrating an example of a configuration obtained by the configuration according to Embodiment 10 being partially modified.
Figure 14B:
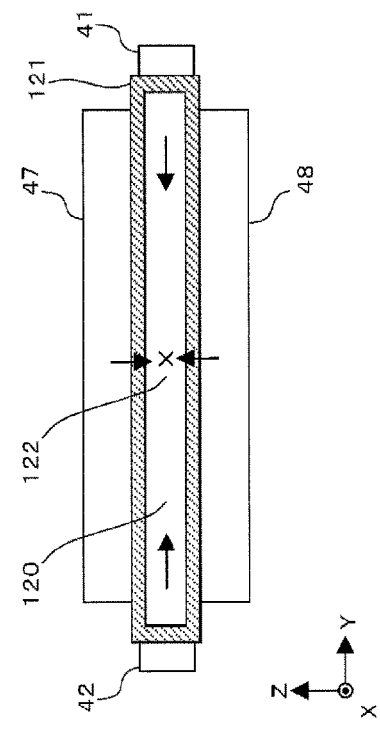
FIG. 14B is a schematic diagram illustrating a portion near the second flow path section according to Embodiment 10 as viewed in the Z-axis negative direction.

As shown in FIGS. 14A and 14B, in Embodiment 10, piezoactuators 47, 48 are disposed in addition to the piezoactuators 41, 42. The piezoactuators 47, 48 are disposed on side surfaces of the member 121 of the second flow path section 120 in the Z-axis positive and negative directions, respectively. The piezoactuators 47, 48 apply ultrasonic waves to the second flow path section 120 to generate an ultrasonic standing wave in the Z-axis direction in the second flow path section 120. By the ultrasonic standing wave, particles that flow in the second flow path section 120 are aligned so as to be close to the central axis 122 also in the Z-axis direction. The two piezoactuators 41, 42 disposed in the Y-axis direction apply acoustic force in the Y-axis direction to particles to align the particles near the central axis. The two piezoactuators 47, 48 disposed in the Z-axis direction apply acoustic force in the Z-axis direction to the particles to align the particles near the central axis.

Thus, since the piezoactuators 47, 48 are disposed also in the Z-axis direction to align the particles, the particles are concentrated near the central axis 122 in both the Y-axis direction and the Z-axis direction. Thus, the particles are concentrated on approximately the same position in the Z-axis direction when passing through the imaging region 51 on the downstream side, and can be easily positioned at the focus position for the particle imaging unit 50. Therefore, the quality of a taken image of the particle can be enhanced.

Ultrasonic standing waves are generated by the piezoactuators 41, 42 in the Y-axis direction, whereby a flat cell included in the measurement sample can be oriented so as to be parallel to the Z-X plane. By the flat cell being thus oriented, the top surface of the flat cell is likely to oppose the particle imaging unit 50, in the imaging region 51 on the downstream side. Therefore, an image of the flat cell can be appropriately taken.

Also in the configuration in FIGS. 14A and 14B, a plurality of sets each including the piezoactuators 47, 48 may be disposed in the X-axis direction. Further, acoustic coupling agents may be provided for the piezoactuators 47, 48. One of the piezoactuators 47, 48 may be replaced with a reflector plate. In a case where an acoustic impedance of the member 121 is higher than an acoustic impedance of a sheath liquid and the measurement sample 12 that flow in the second flow path section 120, one of the piezoactuators 47, 48 may be omitted.

In FIGS. 14A and 14B, an ultrasonic standing wave in the Y-axis direction and an ultrasonic standing wave in the Z-axis direction can be also generated in the second flow path section 120 by only the piezoactuators 41, 42 without providing the piezoactuators 47, 48. In this case, for example, an input signal obtained by a signal component for generating an ultrasonic standing wave in the Y-axis direction, and a signal component for generating an ultrasonic standing wave in the Z-axis direction being superimposed on each other, is applied to the piezoactuators 41, 42. Alternatively, a sine wave signal having a single signal component only is applied to the piezoactuators 41, 42, whereby an ultrasonic standing wave in the Y-axis direction and an ultrasonic standing wave in the Z-axis direction can be generated in the second flow path section 120. In either case, a characteristic of a signal to be applied to the piezoactuators 41, 42 is determined in consideration of an acoustic impedance of the member 121, the length of the second flow path section 120 in the Y-axis direction, the length thereof in the Z-axis direction, and the like.

Figure 14D:
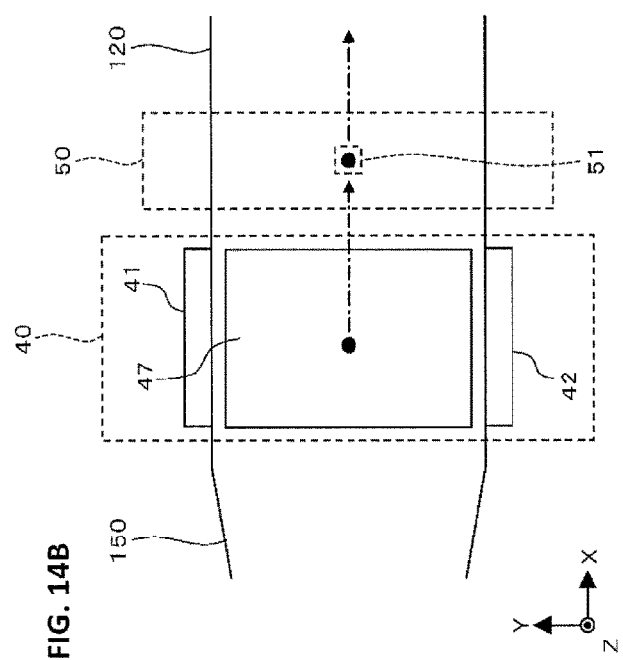
FIG. 14D is a schematic diagram illustrating a portion near a second flow path section in the configuration of this example as viewed in the Z-axis negative direction.

As shown in FIGS. 14C and 14D, by the piezoactuators 47, 48 disposed in the Z-axis direction, acoustic force for concentrating the particles near the central axis 122 in the Y-axis direction, can also be generated. In this case, as shown in FIGS. 14C and 14D, the piezoactuators 41, 42 disposed in the Y-axis direction can be omitted. In order to enhance an acoustic force in the Y-axis direction for concentrating the particles near the central axis 122, the piezoactuators 41, 42 may be further disposed in the Y-axis direction in addition to the piezoactuators 47, 48.

<Embodiment 11>

Figure 15A:
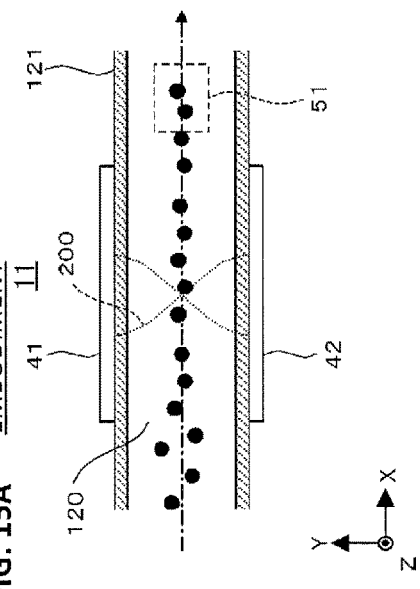
FIGS. 15A and 15B are schematic diagrams illustrating a cross-section of a second flow path section according to Embodiment 11.
Figure 15B:
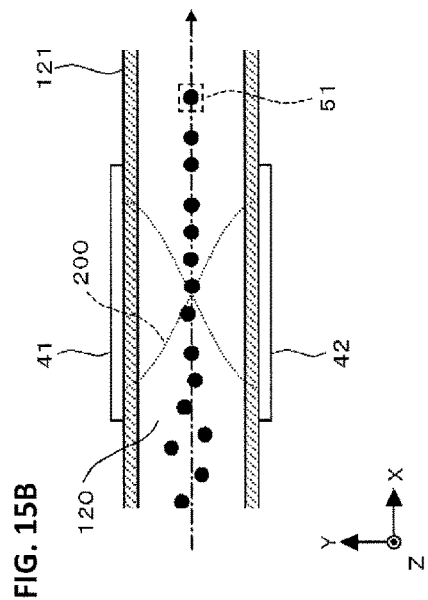

As shown in FIGS. 15A and 15B, in Embodiment 11, an amplitude of an ultrasonic standing wave 200 generated in the second flow path section 120 can be changed. The amplitude of the ultrasonic standing wave 200 can be changed by adjusting an amplitude of an input signal applied to the piezoactuator 41, 42. When the amplitude of the input signal applied to the piezoactuators 41, 42 is increased, the amplitude of the ultrasonic standing wave 200 is increased. When the amplitude of the input signal applied to the piezoactuator 41, 42 is reduced, the amplitude of the ultrasonic standing wave 200 is reduced.

FIG. 15A illustrates a case where the amplitude of the ultrasonic standing wave 200 is low, and FIG. 15B illustrates a case where the amplitude of the ultrasonic standing wave 200 is high. The higher the amplitude of the ultrasonic standing wave 200 is, the more easily particles can be concentrated near the central axis 122. For example, in a case where an imaging magnification of the particle imaging unit 50 is enhanced and a highly accurate image of one particle is taken, the imaging region 51 is reduced according to the imaging magnification being increased as shown in FIG. 15B. In this case, the amplitude of the ultrasonic standing wave 200 is increased such that particles can be aligned at the central axis with enhanced precision. Thus, the particles assuredly pass through the imaging region 51, and omission of image-taking can be reduced. Meanwhile, as shown in FIG. 15A, in a case where the imaging magnification is reduced and an image of a widened range is taken, since the imaging region 51 is wide, particles need not be concentrated near the central axis 122 with high precision. In this case, the amplitude of the ultrasonic standing wave 200 is reduced, and the particles may be aligned near the central axis.

By changing the amplitude of the ultrasonic standing wave 200, a speed at which the measurement sample flows in the second flow path section 120 can be changed. The higher the amplitude of the ultrasonic standing wave 200 is, the lower the speed at which the measurement sample flows in the second flow path section 120 is. Therefore, in the case shown in FIG. 15B, the speed of the measurement sample can be made lower than that in the case shown in FIG. 15A. Therefore, in the case shown in FIG. 15B, an image of a particle can be taken with enhanced accuracy.

Figure 15C:
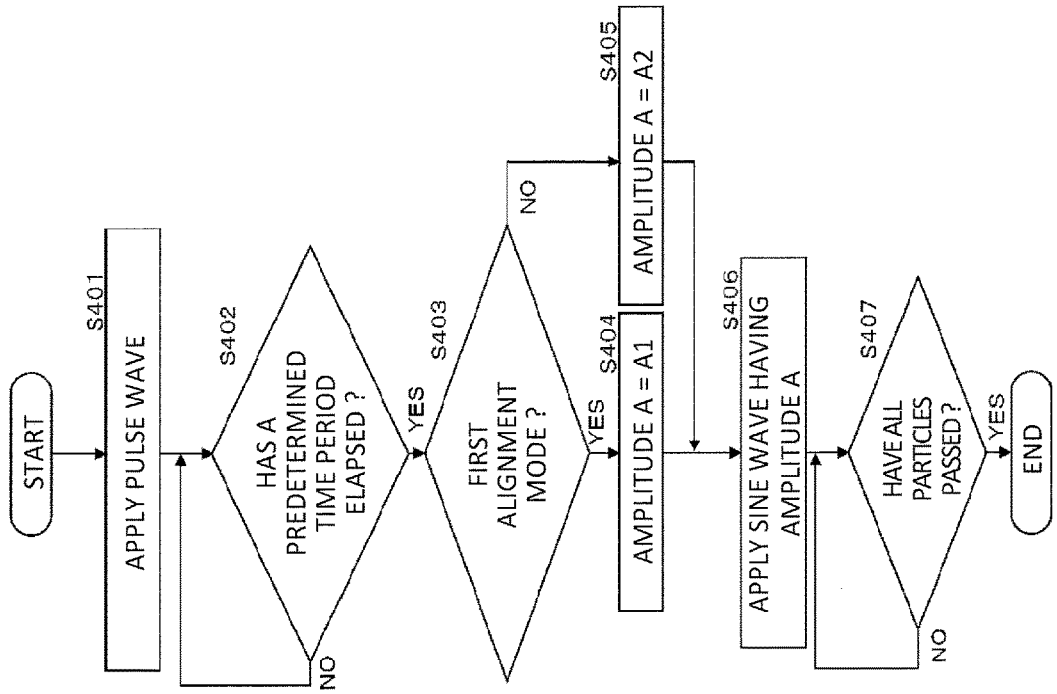
FIG. 15C is a flow chart showing control of a particle alignment unit according to Embodiment 11.

The controller 13 executes, for example, the process shown in FIG. 15C. The controller 13 executes process steps of steps S401, S402 as preprocessing of the control for aligning particles. In step S401, the controller 13 causes an input signal of a pulse wave to be applied to the piezoactuators 41, 42. Bubbles or the like that are adhered to the inner wall of the second flow path section 120 when the measurement sample and the sheath liquid are introduced, are separated from the inner wall of the second flow path section 120 and flow downstream by acoustic force generated by the pulse wave. The controller 13 causes the input signal of the pulse wave to be continuously applied to the piezoactuators 41, 42 until a predetermined time period is determined to have elapsed in step S402. By the bubbles or the like being removed, an ultrasonic standing wave can be stably generated in the second flow path section 120 in shifting to step S403.

When the determination in step S402 is YES, the controller 13 determines in step S403 whether or not an alignment mode set in the particle imaging apparatus 10 is a first alignment mode. In Embodiment 11, an alignment mode can be set selectively as the first alignment mode or a second alignment mode. The first alignment mode is a mode in which particles are aligned near the central axis with a normal precision. The second alignment mode is a mode in which particles are aligned near the central axis with a precision higher than that in the first alignment mode. A user sets the alignment mode through the input unit 16 shown in FIG. 4.

When the determination in step S403 is YES, the controller 13 sets, as an amplitude A1, an amplitude A of an input signal of a sine wave to be applied to the piezoactuators 41, 42, in step S404. When the determination in step S403 is NO, the controller 13 sets, as an amplitude A2, the amplitude A of an input signal of a sine wave to be applied to the piezoactuators 41, 42, in step S405. The amplitude A2 is an amplitude corresponding to the second alignment mode and is higher than the amplitude A1 corresponding to the first alignment mode. The controller 13 causes the input signal of the sine wave having the amplitude A to be applied to the piezoactuators 41, 42, in step S406.

When the amplitude A is set as the amplitude A1, an amplitude of the ultrasonic standing wave 200 is low as shown in, for example, FIG. 15A. In this case, precision for concentrating particles in the Y-axis direction is low. When the amplitude A is set as the amplitude A2, the amplitude of the ultrasonic standing wave 200 is high as shown in, for example, FIG. 15B. In this case, precision for concentrating particles in the Y-axis direction is high.

Thereafter, the controller 13 determines in step S407 whether or not all the particles have passed through the second flow path section 120. When the determination in step S407 is YES, the controller 13 stops application of the input signal to the piezoactuators 41, 42, and ends the process.

In Embodiment 11, the amplitude A of the input signal applied to the piezoactuators 41, 42 is switched, whereby precision for aligning particles that flow in the second flow path section 120 can be changed. In Embodiment 11, the amplitude A of the input signal is switched between two kinds of amplitudes. However, the amplitude A may be switched between three or more amplitudes, and three or more kinds of precision for aligning particles may be set. Further, in the flow chart in FIG. 15C, when the determination in step S407 is NO, the process may be returned to step S403 and determination of the alignment mode may be performed again. Thus, a user is allowed to change the alignment mode during processing for one measurement sample.

Signals applied to the piezoactuators 41, 42 may represent rectangular waves or composite waves having a plurality of frequency components as well as pulse waves and sine waves, as appropriate. The process steps of steps S401, S402 may be additionally performed as steps preceding step S121 or step S122 in FIG. 5C.

<Embodiment 12>

Figure 16C:
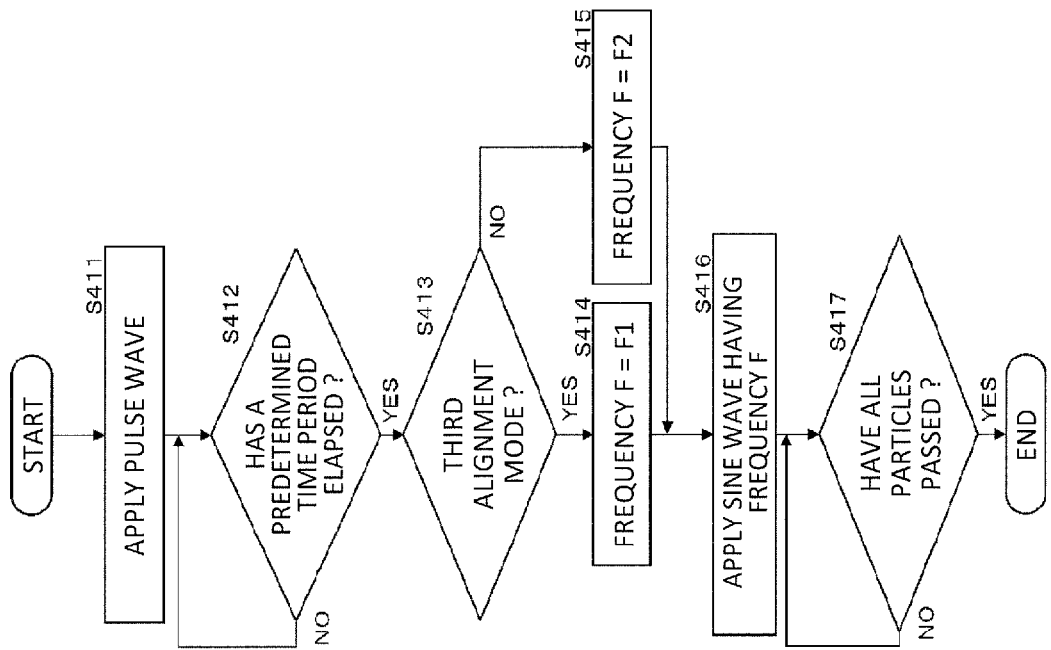
FIG. 16C is a flow chart showing control of a particle alignment unit according to Embodiment 12.
Figure 16A:
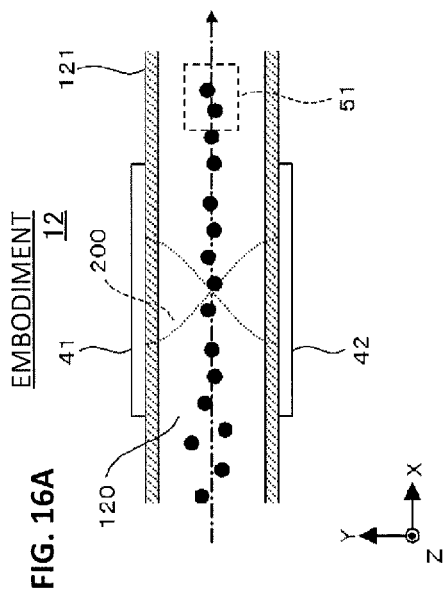
FIGS. 16A and 16B are schematic diagrams illustrating a cross-section of a second flow path section according to Embodiment 12.
Figure 16B:
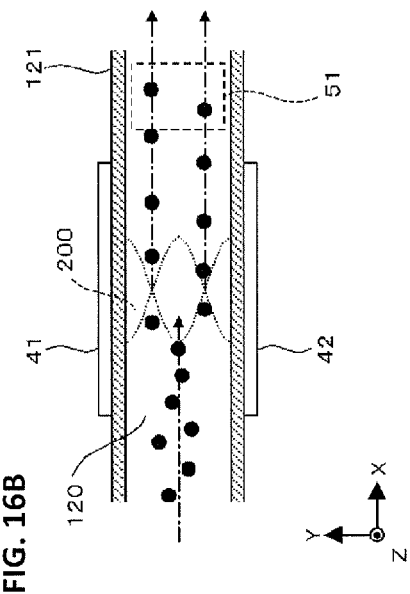

As shown in FIGS. 16A and 16B, in Embodiment 12, the number of nodes of the ultrasonic standing wave 200 generated in the second flow path section 120 can be changed. The number of nodes of the ultrasonic standing wave 200 can be changed by adjusting a frequency of an input signal applied to the piezoactuators 41, 42. The frequency of the input signal applied to the piezoactuators 41, 42 is enhanced, whereby the number of nodes of the ultrasonic standing wave 200 can be increased.

FIG. 16A illustrates a case where the number of nodes of the ultrasonic standing wave 200 is one. FIG. 15B illustrates a case where the number of nodes of the ultrasonic standing wave 200 is two. In a case where the number of nodes of the ultrasonic standing wave 200 is one, particles are aligned near the central axis 122 as shown in FIG. 16A. In this case, in a case where particles flow into the second flow path section 120 in a state where the particles are close to each other, an image of the particles overlapping each other is likely to be taken. As shown in FIG. 16B, in a case where the number of nodes of the ultrasonic standing wave 200 is set as two and the flow of particles is dispersed into two, the particles can be separated into two paths even if the particles flow into the second flow path section 120 in a state where the particles are close to each other. Thus, an image of the particles can be inhibited from being taken in a state where the particles overlap each other.

When the number of nodes of the ultrasonic standing wave is two, the imaging region 51 needs to be widened as shown in FIG. 16B. Instead of the imaging region 51 being widened, the imaging regions may be set for the two paths generated by the two nodes, respectively, of the ultrasonic standing wave 200.

The controller 13 executes a process shown in, for example, FIG. 16C. The controller 13 executes process steps of steps S411, S412 as preprocessing of the control for aligning particles. The process steps of steps S411, S412 are the same as the process steps of steps S401, S402 in FIG. 15C. By the process steps of steps S411, S412, bubbles or the like adhered to the inner wall of the second flow path section 120 are removed.

Thereafter, the controller 13 determines in step S413 whether or not the alignment mode set in the particle imaging apparatus 10 is a third alignment mode. In Embodiment 12, an alignment mode can be set selectively as the third alignment mode or a fourth alignment mode. The third alignment mode is a mode in which particles are aligned near the central axis as shown in FIG. 16A. The second alignment mode is a mode in which particles are separated into two paths and aligned as shown in FIG. 16B. A user sets the alignment mode through the input unit 16 shown in FIG. 4.

When the determination in step S413 is YES, the controller 13 sets, as a frequency F1, a frequency F of an input signal of a sine wave to be applied to the piezoactuators 41, 42, in step S414. When the determination in step S413 is NO, the controller 13 sets, as a frequency F2, the frequency F of the input signal of the sine wave to be applied to the piezoactuators 41, 42, in step S415. The frequency F2 is a frequency corresponding to the fourth alignment mode, and is higher than the frequency F1 corresponding to the third alignment mode. The controller 13 causes the input signal of the sine wave having the frequency F to be applied to the piezoactuators 41, 42, in step S416.

When the frequency F is set as the frequency F1, the number of nodes of the ultrasonic standing wave 200 is one as shown in, for example, FIG. 16A. In this case, positions in the Y-axis direction at which particles are aligned, are near the central axis. When the frequency F is set as the frequency F2, the number of nodes of the ultrasonic standing wave 200 is two as shown in, for example, FIG. 16C. In this case, positions in the Y-axis direction at which particles are aligned are near the two paths which extend in the X-axis direction from the positions of the two nodes, respectively.

Thereafter, the controller 13 determines in step S417 whether or not all the particles have passed through the second flow path section 120. When the determination in step S417 is YES, the controller 13 stops application of input signals to the piezoactuators 41, 42 and ends the process.

In Embodiment 12, the frequency F of the input signal applied to the piezoactuators 41, 42 is changed, whereby the number of alignments of particles that flow in the second flow path section 120 can be changed. In Embodiment 12, the frequency F of the input signal is switched between two kinds of frequencies. However, the frequency F may be switched between three or more frequencies, and the number of alignments of particles may be set as three or more. Further, when the determination in step S417 is NO in the flow chart in FIG. 16C, the process may be returned to step S413 and determination of the alignment mode may be performed again. Thus, a user is allowed to change the alignment mode during processing for one measurement sample.

<Embodiment 13>

A detection target particle is not limited to a CTC. When a disease condition is determined and administration is confirmed, for example, taking images of and detection of a vascular endothelial cell (CEC: circulating endothelial cell), a vascular endothelial progenitor cell (EPC: endothelial progenitor cell), a mesenchymal stem cell (MSC), a hematopoietic stem cell (HSC), an antigen-specific T-cell, or the like are also useful. Such a cell can be detected by an antibody labeled with fluorescence being specifically bound to a surface antigen expressed in each cell. The detection target cell is detected by analyzing an image taken by the particle imaging unit 50, as in Embodiment 1.

In Embodiment 13, a position of a signaling molecule in a detection target cell is confirmed, whereby an activated state of the detection target cell can be determined. The signaling molecule can be a molecule that enables, by its behavior, evaluation of a functionality of the detection target cell. By an antibody labeled with fluorescence being specifically bound to a signaling molecule, the signaling molecule is detected. The position of the detected signaling molecule is confirmed, whereby an activated state or the like of the detection target cell can be determined. Detection of the signaling molecule and determination of the activated state or the like can be performed by analyzing images taken by the particle imaging unit 50.

A dye used in fluorescence-labeling for each of a detection target cell and a signaling molecule, may be a dye described as an example in Embodiment 1, or may be another dye. The reagents 14a to 14g used in the sample preparation unit 14 are changed according to an antibody and a dye to be used for fluorescence-labelling. Further, a wavelength of light for excitation of the dyes may be a single wavelength as in Embodiment 1, or may include different wavelengths. When wavelengths for excitation of the dyes for obtaining fluorescences are different, the light source 501 shown in FIG. 3B is, for example, a multi-light emitting laser.

Also in Embodiment 13, detection target cells are firstly sorted according to the flow charts in FIGS. 5A and 5B, similarly to Embodiment 1.

When the detection target cell is a vascular endothelial cell, a vascular endothelial progenitor cell, or a mesenchymal stem cell, the sample preparation unit 14 mixes predetermined reagents with the blood specimen 11 in step S101 in FIG. 5A. The reagents to be mixed here are a reagent for hemolyzing red blood cells, a reagent including a labeled CD45 antibody for detecting white blood cells, a reagent including an antibody that is labeled with fluorescence by a dye and specifically binds to a surface antigen expressed on a detection target cell, a reagent including an antibody that is labeled with fluorescence by a dye and specifically binds to a signaling molecule, and a reagent for staining a nucleus.

Similarly to Embodiment 1, a reagent for hemolyzing red blood cells may be omitted.

In step S104 in FIG. 5A, the controller 13 executes a process similar to that in Embodiment 1. When the intensity of a fluorescence signal is lower than or equal to a predetermined threshold value, and the intensity of a forward scattered light signal is higher than or equal to a predetermined threshold value, the controller 13 determines that the particle at the light application position 21 is highly likely to be a detection target cell, that is, a vascular endothelial cell, a vascular endothelial progenitor cell, or a mesenchymal stem cell. When the particle is a detection target cell, the particle does not bind to the labeled CD45 antibody, whereby the intensity of the fluorescence signal is lower than or equal to the predetermined value. In step S104, when the particle is other than white blood cells and the size of the particle is great, the controller 13 determines that the particle is highly likely to be a detection target cell, that is, a vascular endothelial cell, a vascular endothelial progenitor cell, or a mesenchymal stem cell.

When the detection target cell is a hematopoietic stem cell, the sample preparation unit 14 mixes, with the blood specimen 11, a reagent for hemolyzing red blood cells, a reagent including labeled antibodies for detecting all blood cells differentiated from a hematopoietic stem cell, a reagent including an antibody that is labeled with fluorescence by a dye and specifically binds to a surface antigen expressed on the hematopoietic stem cell, a reagent including an antibody that is labeled with fluorescence by a dye and specifically binds to a signaling molecule in the hematopoietic stem cell, and a reagent for staining a nucleus, in step S101 in FIG. 5A. The reagent that includes labeled antibodies for detecting all blood cells differentiated from a hematopoietic stem cell is called a Lineage marker in general. In the description herein, the antibodies in the Lineage marker are labeled by using the same dye. Similarly to Embodiment 1, a reagent for hemolyzing red blood cells may be omitted.

In step S104 in FIG. 5A, when the intensity of a fluorescence signal is lower than or equal to a predetermined threshold value, and the intensity of a forward scattered light signal is higher than or equal to a predetermined threshold value, the controller 13 determines that the particle at the light application position 21 is highly likely to be a detection target cell, that is, a hematopoietic stem cell. The dichroic mirror 207 and the spectral filter 209 shown in FIG. 3A are adjusted so as to guide the fluorescence based on the Lineage marker, toward the light detector 210. When the particle is a detection target cell, the particle does not bind to the Lineage marker, whereby the intensity of the fluorescence signal is lower than or equal to the predetermined value. Further, the hematopoietic stem cell is larger than any of the other blood cells differentiated from the hematopoietic stem cell. Therefore, in step S104, when the intensity of the fluorescence signal is lower than or equal to the predetermined threshold value, and the intensity of the forward scattered light signal is higher than or equal to the predetermined threshold value, the particle at the light application position 21 is highly likely to be a hematopoietic stem cell.

When the detection target cell is an antigen-specific T-cell, the sample preparation unit 14 mixes, with the blood specimen 11, a reagent for hemolyzing red blood cells, a reagent obtained by excluding CD2, CD3 antibodies from the Lineage marker, a reagent including a labeled CD3 antibody that specifically binds to a surface antigen expressed on a T-cell, a reagent including an MHC tetramer that is labeled by a dye and specifically binds to a surface antigen expressed on an antigen-specific T-cell among T-cells, a reagent including an antibody that is labeled with fluorescence by a dye and specifically binds to a signaling molecule in the antigen-specific T-cell, and a reagent for staining a nucleus, in step S101 in FIG. 5A. In the description herein, the antibodies obtained by excluding CD2, CD3 from the Lineage marker are labeled by using the same dye. Similarly to Embodiment 1, a reagent for hemolyzing red blood cells may be omitted.

In step S104 in FIG. 5A, when the intensity of a fluorescence signal is lower than or equal to a predetermined threshold value, the controller 13 determines that the particle at the light application position 21 is highly likely to be a T-cell. The dichroic mirror 207 and the spectral filter 209 shown in FIG. 3A are adjusted so as to guide the fluorescence based on the Lineage marker, toward the light detector 210, as in the case of detection of the hematopoietic stem cell. When the particle is a T-cell, the particle does not bind to the Lineage marker, whereby the intensity of the fluorescence signal is lower than or equal to the predetermined value. Therefore, in step S104, when the intensity of the fluorescence signal is lower than or equal to the predetermined threshold value, the particle at the light application position 21 is highly likely to be a T-cell.

Thus, the controller 13 executes the process in FIG. 5B on the particle for which whether or not the particle is highly likely to be a detection target cell has been determined. In step S112 in FIG. 5B, the controller 13 determines whether or not a particle positioned in the particle sorting unit 30 is highly likely to be a detection target cell. The controller 13 causes the particle determined to be highly likely to be a detection target cell to flow through the fifth flow path section 150 into the second flow path section 120. The controller 13 executes the process in FIG. 5C to sequentially take images of the particles determined to be highly likely to be detection target cells.

In the above processes, the controller 13 stores, in the storage unit 15, the images of the particle that is highly likely to be a detection target cell, that is, a vascular endothelial cell, a vascular endothelial progenitor cell, a mesenchymal stem cell, a hematopoietic stem cell, or an antigen-specific T-cell. The images stored in the storage unit 15 include an image of fluorescence of the labeled antibody that specifically binds to a surface antigen expressed on the detection target cell, an image of fluorescence of the labeled antibody that specifically binds to a signaling molecule in the detection target cell, and a bright field image of the particle. In taking of an image, the light source 501 shown in FIG. 3B applies, to the imaging region 51, light for excitation for obtaining fluorescence by the dye of each labeled antibody. The camera 504 receives fluorescences that have different wavelengths and are generated from the labeled antibodies, and outputs image information for each fluorescence. The camera 505 receives light that has been transmitted through the particle, and outputs bright field image information. In the storage unit 15, image information from the cameras 504, 505 is stored.

When the imaging process has been ended, an operator inputs an instruction for displaying a result, through the input unit 16, to the particle imaging apparatus 10.

As shown in FIG. 17A, in step S211, the controller 13 determines whether or not the operator has inputted an instruction for displaying a result. When the determination in step S211 is YES, the controller 13 analyzes images of all the particles of which the images have been taken, and extracts the detection target cells, in step S212.

When the detection target cell is a vascular endothelial cell, a vascular endothelial progenitor cell, a mesenchymal stem cell, or a hematopoietic stem cell, the controller 13 refers to an image of a labeling dye which specifically binds to an antibody expressed on the detection target cell, for each particle, and determines whether or not the image includes a region in which the intensity of fluorescence exceeds a predetermined intensity, in step S212. When the image includes the region of the fluorescence, the controller 13 determines that the determination target particle is a detection target cell. When the image does not include the region of the fluorescence, the controller 13 determines that the determination target particle is not a detection target cell.

When the detection target cell is an antigen-specific T-cell, the controller 13 firstly refers to an image of a CD3 labeling dye which specifically binds to an antibody expressed on a T-cell, for each particle, and determines whether or not the image includes a region in which the intensity of fluorescence exceeds a predetermined intensity, in step S212. When the image includes the region of the fluorescence, the controller 13 determines that the determination target particle is a T-cell. When the image does not include the region of the fluorescence, the controller 13 determines that the determination target particle is not a T-cell. Further, the controller 13 refers to an image of a dye for labeling MHC tetramer that binds to a surface antigen expressed on an antigen-specific T-cell, for each particle determined to be a T-cell, and determines whether or not the image includes a region in which the intensity of fluorescence exceeds a predetermined intensity. When the image includes the region of the fluorescence, the controller 13 determines that the determination target particle is an antigen-specific T-cell. When the image does not include the region of the fluorescence, the controller 13 determines that the determination target particle is not an antigen-specific T-cell.

Further, in step S213, the controller 13 analyzes the images of the extracted detection target cells, determines whether or not the cells have been activated, for each cell, and extracts activated detection target cells. The controller 13 detects a state of a signaling molecule in the cell with reference to the image of the labeling dye which specifically binds to the signaling molecule. The controller 13 determines whether or not the detection target cell has been activated, on the basis of the detected state of the signaling molecule.

For example, when the detection target cell is a vascular endothelial cell (CEC), the signaling molecule can be NFκB. In step S213, the controller 13 determines whether or not the vascular endothelial cell has been activated by determining whether or not NFκB that is the signaling molecule is localized in the nucleus. The vascular endothelial cell separates from the inner wall of blood vessels and flows into blood. The separation of the vascular endothelial cell is caused not only by inflammatory stimuli but also by change of pressure due to compression or the like. The controller 13 identifies the separation caused by inflammatory stimuli among separations caused by the above-mentioned reasons, according to whether or not NFκB that is the signaling molecule is localized in the nucleus. The controller 13 extracts the vascular endothelial cell having been separated by the inflammatory stimuli, as an activated vascular endothelial cell.

As shown in FIG. 18A, in the vascular endothelial cell having been separated by the inflammatory stimuli, NFκB tends to be localized in the nucleus. In the left figure in FIG. 18A, a fluorescence image of the nucleus is shown. In the left figure in FIG. 18A, for convenience, dotted lines representing the outline of the nucleus are added. In the right figure in FIG. 18A, a fluorescence image of NFκB that is the signaling molecule is shown. Further, a region corresponding to the nucleus in the left figure is indicated by dotted lines. In both the left figure and the right figure in FIG. 18A, the darker the black color is, the higher the intensity of each of the fluorescence from the nucleus and the fluorescence from NFκB is. In the example in FIG. 18A, it can be found that NFκB that is the signaling molecule is localized in the nucleus.

In the example in FIG. 18B, NFκB that is the signaling molecule is not localized in the nucleus. In the right figure in FIG. 18B, a region represented by dotted lines is a region of the nucleus. Thus, in the vascular endothelial cell having been separated by stimuli other than inflammatory stimuli, NFκB is less likely to be localized in the nucleus. The controller 13 analyzes the image of the fluorescence of the signaling molecule, and determines whether or not NFκB that is the signaling molecule is localized in the nucleus, thereby determining whether or not the vascular endothelial cell has been activated. Also in a case where a detection target cell is a vascular endothelial progenitor cell, a mesenchymal stem cell, a hematopoietic stem cell, or an antigen-specific T-cell, the controller 13 similarly evaluates functionality of the cells on the basis of the localization position of the signaling molecule, and extracts, as activated cells, cells of which the number has been increased due to injury or the like. For example, in a case where a detection target cell is a vascular endothelial progenitor cell or a mesenchymal stem cell, the controller 13 evaluates repairing ability of the cells on the basis of the localization position of the signaling molecule, and extracts the cell having high repairing ability as the activated cell.

The functionality of the detection target cell may be evaluated on the basis of not only the localization position of the signaling molecule but also other elements. The type of the signaling molecule can be changed as appropriate according to the element used for evaluating the functionality.

In step S213, the controller 13 causes the output unit 17 to display the number of detection target cells extracted in step S212 and the number of activated detection target cells, and further causes the output unit 17 to display images of the detection target cell in step S214. For example, when a detection target cell is a vascular endothelial cell (CEC), a screen 60 shown in FIGS. 17B and 17C is displayed on the output unit 17 in steps S213, S214.

On the screen 60, the number of vascular endothelial cells (CECs), the number of activated vascular endothelial cells (CECs), and images of the vascular endothelial cell (CEC) are displayed. An operator can know whether or not the vascular endothelial cell has been increased in the blood with reference to the number of the vascular endothelial cells (CECs). Further, the proportion of the vascular endothelial cells in the activated state can be known with reference to the number of the activated vascular endothelial cells (CECs). Such information can be useful for determining a plan of treatment by a doctor and the like.

The two images that are laterally aligned are for the same particle. An image 66 represents fluorescence generated by a labeled antibody that specifically binds to the nucleus, and an image 67 represents fluorescence generated by a labeled antibody that specifically binds to the signaling molecule. As described above, the signaling molecule is NFκB that is a protein included in the vascular endothelial cell. For detecting the vascular endothelial cell, a labeled CD146 antibody that specifically binds to an antigen expressed on the vascular endothelial cell, is used. The images 66, 67 are obtained by reversing the gradation and then performing conversion to gray scale images. In addition to the images 66, 67, a bright field image may be further included in the screen 60.

The image of the particle shown in FIG. 17B represents an activated vascular endothelial cell, and the image of the particle shown in FIG. 17C represents an unactivated vascular endothelial cell. In a case where the number of the images of the particle of the vascular endothelial cell is plural, an operator is allowed to switch between the images of the particle on the screen 60 and perform display thereon. Further, a button or the like that allows an image of an activated vascular endothelial cell and an image of an unactivated vascular endothelial cell to be individually displayed, may be separately provided on the screen 60.

In Embodiment 13, images of cells useful for determining a disease condition and confirming administration, such as images of a vascular endothelial cell, a vascular endothelial progenitor cell, a mesenchymal stem cell, a hematopoietic stem cell, or an antigen-specific T-cell, as well as images of CTCs, are obtained. The images of these cells are displayed together with the number of extracted cells according to an operator's request. A doctor and the like can use the displayed information for determining a plan of treatment.

For example, a patient who suffers from myocardial infarction or cerebral infarction, has an increased number of vascular endothelial cells as compared to healthy persons. Further, if tissues are damaged, the number of vascular endothelial progenitor cells and the number of mesenchymal stem cells are increased as compared to those of healthy persons. Therefore, when a doctor and the like recognize the numbers of these cells, the doctor and the like can recognize a likelihood that a patient suffers from a disease such as myocardial infarction, or a likelihood that tissues of a patient are damaged.

Further, in Embodiment 13, an activated state of a vascular endothelial cell, a vascular endothelial progenitor cell, a mesenchymal stem cell, a hematopoietic stem cell, or an antigen-specific T-cell is detected on the basis of a behavior of a signaling molecule, and displayed. Thus, an activated state of a detection target cell is further displayed, whereby specificity in a result of detection of a detection target cell can be further enhanced. For example, in a case where a detection target cell is a vascular endothelial cell, the number of vascular endothelial cells (CECs) and the number of activated vascular endothelial cells (CECs) are displayed as shown in FIGS. 17B and 17C. Thus, a doctor and the like can accurately recognize the number of vascular endothelial cells having been separated by inflammatory stimuli, and can more appropriately recognize a likelihood that a patient suffers from a disease such as myocardial infarction. Further, recently, a T-cell that responds to a specific antigen is used in immunotherapy. For example, a therapeutic method in which a T-cell that can respond specifically to a cancer cell is returned into blood and the effect thereof is monitored, is being attempted. In Embodiment 13, in this monitoring, the activated state of the antigen-specific T-cell can be presented to a doctor and the like by the number of cells and the images thereof. Thus, the doctors and the like can confirm the effect of the immunotherapy.

<Embodiment 14>

As shown in FIG. 19, an intermediate flow path section that connects between the first flow path section 110 and the second flow path section 120 may further include a ninth flow path section 171 and a tenth flow path section 172 in addition to the fifth flow path section 150. The tenth flow path section 172 is an expanded flow path section that has a cross-sectional area increased toward the downstream side, similarly to the fifth flow path section 150. A speed of flow of a particle from the first flow path section 110 toward the second flow path section 120 is reduced due to the fifth flow path section 150, and is further reduced due to the tenth flow path section 172.

The ninth flow path section 171 has a rectangular cross-sectional shape similar to that shown in FIG. 2B. The ninth flow path section 171 has a constant cross-sectional area. The tenth flow path section 172 has a rectangular cross-sectional shape. The width in the Z-axis direction on the cross-section of the tenth flow path section 172 is equal to the width in the Z-axis direction on the cross-section of the ninth flow path section 171. The cross-sectional shape of the tenth flow path section 172 is gradually increased along the central axis in the X-axis positive direction. The central axis of the ninth flow path section 171 and the central axis of the tenth flow path section 172 extend in the X-axis direction, and are aligned with the central axis of the fifth flow path section 150 and the central axis of the second flow path section 120.

The cross-sectional shape of the tenth flow path section 172 is gradually increased in the X-axis positive direction. Therefore, the cross-sectional area of the second flow path section 120 is greater as compared to that in the case shown in FIG. 2B. The cross-sectional shape of the second flow path section 120 has a width expanded in Y-axis direction as compared to that in FIG. 2B. The width of the second flow path section 120 in the Z-axis direction is equal to that in the case shown in FIG. 2B.

In Embodiment 14, as described above, the cross-sectional area of the second flow path section 120 is further increased due to the tenth flow path section 172. Therefore, a speed at which a particle flows in the second flow path section 120 can be further reduced. Specifically, the speed at which a particle flows in the first flow path section 110 is 1.0 m/s, whereas the speed at which the particle flows in the second flow path section 120 can be reduced to about 0.01 m/s. In this case, the speed at which a particle flows in the second flow path section 120 is about 1/100 of the speed at which the particle flows in the first flow path section 110. Therefore, even when the speed at which a particle flows in the first flow path section 110 is increased in order to extract an imaging target particle from a lot of particles, the speed at which the particle flows in the second flow path section 120 is significantly reduced, whereby a more accurate image of the particle can be taken by the particle imaging unit 50. That is, an image of an imaging target particle can be taken with enhanced quality while the processing speed of the particle imaging apparatus 10 is maintained.

In Embodiment 14, the width of the second flow path section 120 in the Y-axis direction is increased. Therefore, as shown in FIG. 19, when particles are aligned by the particle alignment unit 40, acoustic force outputted from the particle alignment unit 40 needs to be enhanced.

In order to reduce, to about 0.01 m/s, the speed at which a particle flows in the second flow path section 120, the intermediate flow path section that connects between the first flow path section 110 and the second flow path section 120 may include ninth flow path sections 171a, 171b and tenth flow path sections 172a, 172b, as shown in FIG. 20. In this case, the width, in the Y-axis direction, of the second-stage ninth flow path section 171b disposed on the downstream side is less than that of the second flow path section 120. Therefore, as shown in FIG. 20, by the particle alignment unit 40 being disposed in the second-stage ninth flow path section 171b, the particles can be aligned without significantly enhancing acoustic force. Thus, turbulence in the flow of the particles due to the second flow path section 120 can be inhibited.

An arrangement in which the particle alignment unit 40 is disposed in the ninth flow path section 171 other than the arrangement in which the particle alignment unit 40 is disposed in the second flow path section 120 as shown in FIG. 19, may be employed. In a case where the particle alignment unit 40 is disposed in the ninth flow path section 171, since the width of the ninth flow path section 171 in the Y-axis direction is less than that of the second flow path section 120, the particles can be aligned without significantly enhancing acoustic force outputted from the particle alignment unit 40. In a case where the particle alignment unit 40 is disposed in the ninth flow path section 171, the particle alignment unit 40 is preferably disposed as close to the downstream end as possible. The particle alignment units 40 may be disposed in both the second flow path section 120 and the ninth flow path section 171. In the configuration shown in FIG. 20, the particle alignment units 40 may be further disposed in all of or any one or two of the second flow path section 120 and the ninth flow path sections 171a, 171b.

In the configurations shown in FIG. 19 and FIG. 20, the length and the width of each of the ninth flow path sections 171, 171a, 171b can be adjusted as appropriate. The degree of expansion of each of the tenth flow path sections 172, 172a, 172b can also be adjusted as appropriate. The ninth flow path sections 171, 171a, 171b may be set so as to be very short, or the ninth flow path sections 171, 171a, 171b may be omitted.

<Embodiment 15>

Figure 21:
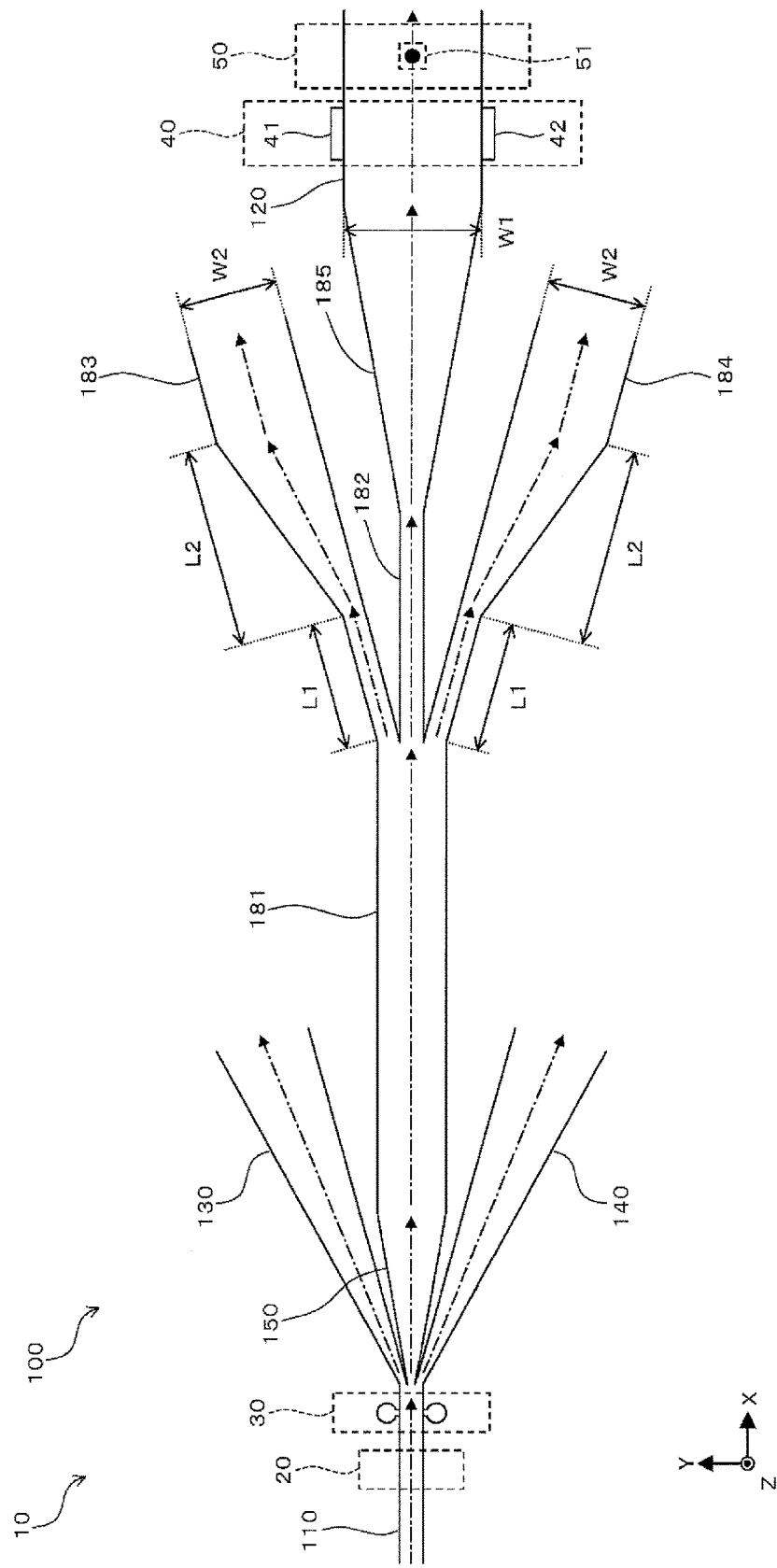
FIG. 21 is a schematic diagram illustrating a configuration of a particle imaging apparatus according to Embodiment 15 as viewed in the Z-axis negative direction.

As shown in FIG. 21, an intermediate flow path section that connects between the first flow path section 110 and the second flow path section 120 may further include an eleventh flow path section 181, a twelfth flow path section 182, and a fifteenth flow path section 185 in addition to the fifth flow path section 150, and, further, the flow path 100 may include a thirteenth flow path section 183 and a fourteenth flow path section 184 as branching flow path sections that branch from the intermediate flow path section, on a side downstream of the third flow path section 130. The fifteenth flow path section 185 is an expanded flow path section that has a cross-sectional area increased toward the downstream side, similarly to the fifth flow path section 150. A speed of flow of a particle from the first flow path section 110 toward the second flow path section 120 is reduced due to the fifth flow path section 150, and the flow rate is thereafter reduced due to the thirteenth flow path section 183 and the fourteenth flow path section 184, and the speed thereof is further reduced due to the tenth flow path section 172.

The cross-sectional shape of the eleventh flow path section 181 is the same as shown in FIG. 2B. The twelfth flow path section 182 has a rectangular cross-sectional shape, and has a shape obtained by dividing the cross-sectional shape shown in FIG. 2B into almost three in the Y-axis direction. The width in the Z-axis direction on the cross-section of the twelfth flow path section 182 is equal to the width of the eleventh flow path section 181 in the Z-axis direction. The twelfth flow path section 182 linearly extends parallel to the X-axis direction. The twelfth flow path section 182 has a constant cross-sectional shape over the entire length of the twelfth flow path section 182.

The fifteenth flow path section 185 that connects to the rear end of the twelfth flow path section 182 also has a rectangular cross-sectional shape. The width in the Z-axis direction on the cross-section of the fifteenth flow path section 185 is equal to the width in the Z-axis direction on the cross-section of the twelfth flow path section 182. The cross-sectional shape of the fifteenth flow path section 185 is gradually widened in the Y-axis direction toward the front in the X-axis positive direction. The central axis of each of the eleventh flow path section 181, the twelfth flow path section 182, and the fifteenth flow path section 185 extends in the X-axis direction, and is aligned with the central axis of the fifth flow path section 150 and the central axis of the second flow path section 120.

The thirteenth flow path section 183 and the fourteenth flow path section 184 are disposed so as to be symmetric about the central axis of the twelfth flow path section 182. The thirteenth flow path section 183 has a rectangular cross-sectional shape and the fourteenth flow path section 184 has a rectangular cross-sectional shape. The cross-sectional shape of the preceding end portion of each of the thirteenth flow path section 183 and the fourteenth flow path section 184 is obtained by dividing the cross-sectional shape shown in FIG. 2B into almost three in the Y-axis direction, similarly to the twelfth flow path section 182. The thirteenth flow path section 183 and the fourteenth flow path section 184 each have a constant cross-sectional shape in a range L1 from a branching position. The thirteenth flow path section 183 and the fourteenth flow path section 184 linearly extend in the range L1. Beyond the range L1, the cross-sectional shape of each of the thirteenth flow path section 183 and the fourteenth flow path section 184 is expanded only in the direction parallel to the X-Y plane in a range L2, and thereafter becomes constant again. In the range L2, the cross-sectional shape of each of the thirteenth flow path section 183 and the fourteenth flow path section 184 is expanded only in the outward direction in which the thirteenth flow path section 183 and the fourteenth flow path section 184 are distant from the twelfth flow path section 182 and the fifteenth flow path section 185.

In the configuration shown in FIG. 21, the length of the range L1 in the flow direction is less than the length of the twelfth flow path section 182 in the flow direction. Instead thereof, the length of the range L1 in the flow direction may be equal to the length of the twelfth flow path section 182 in the flow direction, or may be greater than the length of the twelfth flow path section 182 in the flow direction. Further, in the configuration shown in FIG. 21, a width W2 of a portion downstream of the range L2 of each of the thirteenth flow path section 183 and the fourteenth flow path section 184 is less than the width W1 of the second flow path section 120. Instead thereof, the width W2 may be equal to the width W1, or may be greater than the width W1. Other than these, a branching angle of each of the thirteenth flow path section 183 and the fourteenth flow path section 184 can be adjusted as appropriate. Further, the degree of expansion of each of the thirteenth flow path section 183 and the fourteenth flow path section 184 in the range L2 can be also adjusted as appropriate. The degree of expansion of the fifteenth flow path section 185 can be variously adjusted. The eleventh flow path section 181 may be set so as to be very short, or the eleventh flow path section 181 may be omitted.

A portion of sheath liquid flowing in the eleventh flow path section 181 flows separately into the thirteenth flow path section 183 and the fourteenth flow path section 184. Thus, the flow rate in the twelfth flow path section 182 is reduced. Further, the cross-sectional area of the fifteenth flow path section 185 is gradually increased toward the downstream side, whereby the flow speed of the sheath liquid and the measurement sample 12 that flow in the fifteenth flow path section 185 is gradually reduced.

In the configuration shown in FIG. 21, the flow rate in the twelfth flow path section 182 is reduced due to the thirteenth flow path section 183 and the fourteenth flow path section 184, and the flow speed of the sheath liquid and the measurement sample 12 is thereafter reduced due to the fifteenth flow path section 185. Therefore, a speed at which a particle flows in the second flow path section 120 can be further reduced.

Specifically, in the configuration shown in FIG. 21, a speed at which a particle flows in the first flow path section 110 is 1.0 m/s, whereas a speed at which the particle flows in the second flow path section 120 can be reduced to about 0.01 m/s. In this case, a speed at which a particle flows in the second flow path section 120 is about 1/100 of a speed at which the particle flows in the first flow path section 110. Therefore, even when a speed at which a particle flows in the first flow path section 110 is increased in order to extract an imaging target particle from a lot of particles, a speed at which a particle flows in the second flow path section 120 is significantly reduced, whereby the particle imaging unit 50 can take a more accurate image of the particle. That is, an image of the imaging target particle can be taken with enhanced quality while the processing speed of the particle imaging apparatus 10 is maintained.

Figure 22:
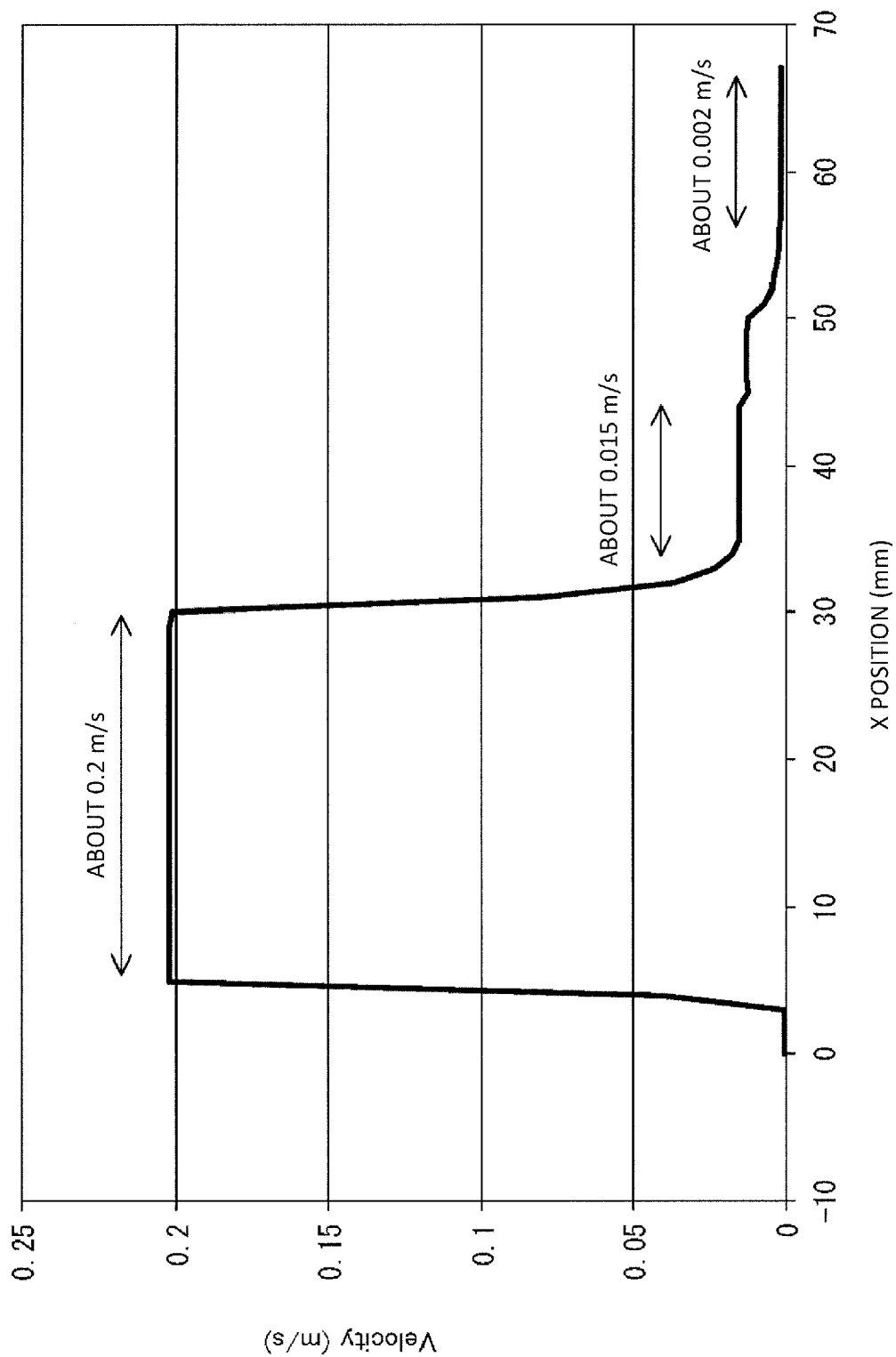
FIG. 22 illustrates a simulation result obtained by analyzing flow speeds in flow path sections, respectively, in the particle imaging apparatus according to Embodiment 15.

FIG. 22 shows a simulation result obtained by analyzing, by the inventors of the present invention, a flow speed at which the measurement sample 12 flows from the first flow path section 110 toward the second flow path section 120 in the configuration shown in FIG. 21. The simulation result in FIG. 22 is obtained by analysis using the flow path 100 having the same shape as shown in FIG. 21. In the simulation in FIG. 22, each of the third flow path section 130 and the fourth flow path section 140 has a rectangular cross-sectional shape that is expanded only in the X-Y plane direction toward the downstream side. The third flow path section 130 and the fourth flow path section 140 do not have constant widths on the downstream side as do the thirteenth flow path section 183 and the fourteenth flow path section 184, and are connected to waste liquid storing units.

In FIG. 22, as flow speeds of the measurement sample 12, about 0.2 m/s, about 0.015 m/s, and about 0.002 m/s are indicated. A range indicated by a double-headed arrow with about 0.2 m/s represents a range of the first flow path section 110. A range indicated by a double-headed arrow with about 0.015 m/s represents a range of the eleventh flow path section 181. A range indicated by a double-headed arrow with about 0.002 m/s represents a range of the second flow path section 120. As illustrated, the simulation result indicates that the flow speed of the measurement sample 12 which is about 0.2 m/s in the first flow path section 110 can be reduced to 1/100 thereof, that is, to about 0.002 m/s. The flow speed is slightly reduced immediately after the range indicated by the double-headed arrow with about 0.015 m/s, since the measurement sample 12 and sheath liquid flow separately into the thirteenth flow path section 183 and the fourteenth flow path section 184.

Further, in the configuration shown in FIG. 21, the thirteenth flow path section 183 and the fourteenth flow path section 184 are configured so as to be symmetric about the central axis of the eleventh flow path section 181. Thus, a sheath liquid flowing in the eleventh flow path section 181 flows almost evenly into the thirteenth flow path section 183 and the fourteenth flow path section 184. Therefore, flow of a particle from the twelfth flow path section 182 through the fifteenth flow path section 185 into the second flow path section 120 is stabilized, and the particle imaging unit 50 is allowed to take a more accurate image.

Further, in the configuration shown in FIG. 21, the width W1 of the second flow path section 120 in the Y-axis direction can be reduced as compared to the configuration in FIG. 20 and FIG. 21. Therefore, acoustic force from the particle alignment unit 40 can be effectively applied to particles, and the particles can be smoothly aligned. The particle alignment unit 40 may be provided also in the eleventh flow path section 181. Further, the width W1 of the second flow path section 120 in the Y-axis direction is small, whereby the particles are less likely to deviate from the central axis in the second flow path section 120. Therefore, in a case where no problem arises in taking of an image, the particle alignment unit 40 may be omitted as appropriate.

In the configuration shown in FIG. 21, each of the thirteenth flow path section 183 and the fourteenth flow path section 184 is expanded in the range L2, and the width W2 is constant on a side downstream of the range L2. Thus, a sheath liquid can be effectively guided to the thirteenth flow path section 183 and the fourteenth flow path section 184, and increase of the flow speed in the twelfth flow path section 182 can be inhibited. For example, in a case where the thirteenth flow path section 183 and the fourteenth flow path section 184 are not expanded in the range L2 and the width of the range L1 is maintained, since the downstream side portion of the twelfth flow path section 182 is expanded due to the fifteenth flow path section 185, flowing in the twelfth flow path section 182 is facilitated as compared to the thirteenth flow path section 183 and the fourteenth flow path section 184. As a result, the flow speed at which the measurement sample 12 flows in the twelfth flow path section 182 becomes higher than the flow speed at which the measurement sample 12 flows in the eleventh flow path section 181, whereby the flow speed of the measurement sample 12 is less likely to be effectively reduced in the second flow path section 120. In the configuration shown in FIG. 21, each of the thirteenth flow path section 183 and the fourteenth flow path section 184 is expanded in the range L2, and the width W2 is thereafter made constant, whereby flowing in each of the thirteenth flow path section 183 and the fourteenth flow path section 184 is facilitated to almost the same degree as flowing in the twelfth flow path section 182. Thus, as examined in FIG. 22, the flow speed at which the measurement sample 12 flows in the second flow path section 120 can be effectively reduced.

Figure 23A:
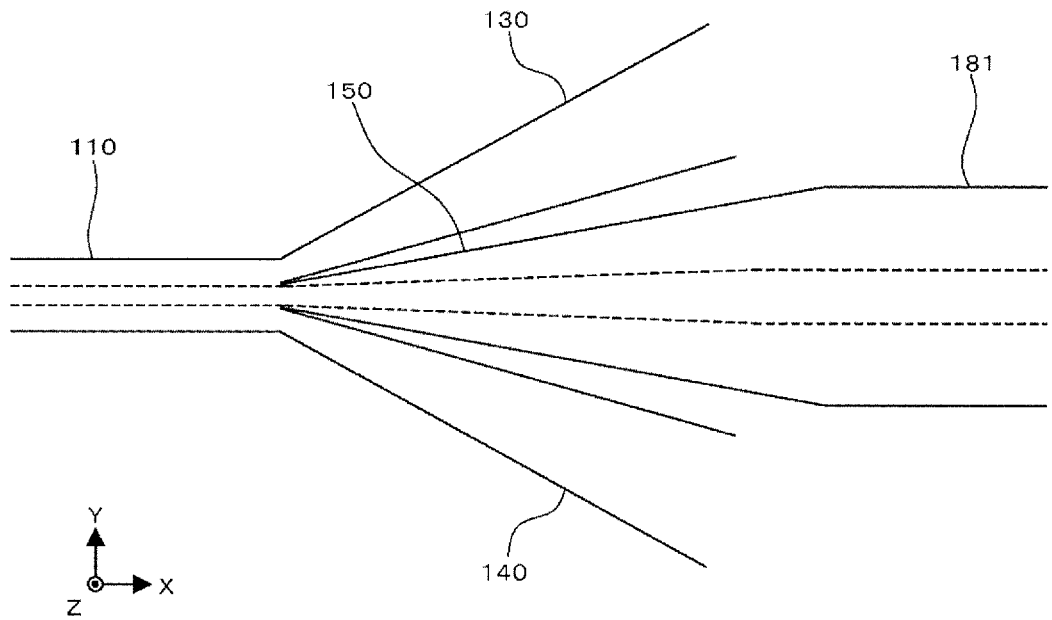
FIGS. 23A and 23B are schematic diagrams illustrating an upstream-side branching portion and a downstream-side branching portion, respectively, in the particle imaging apparatus according to Embodiment 15 as viewed in the Z-axis negative direction.
Figure 23B:
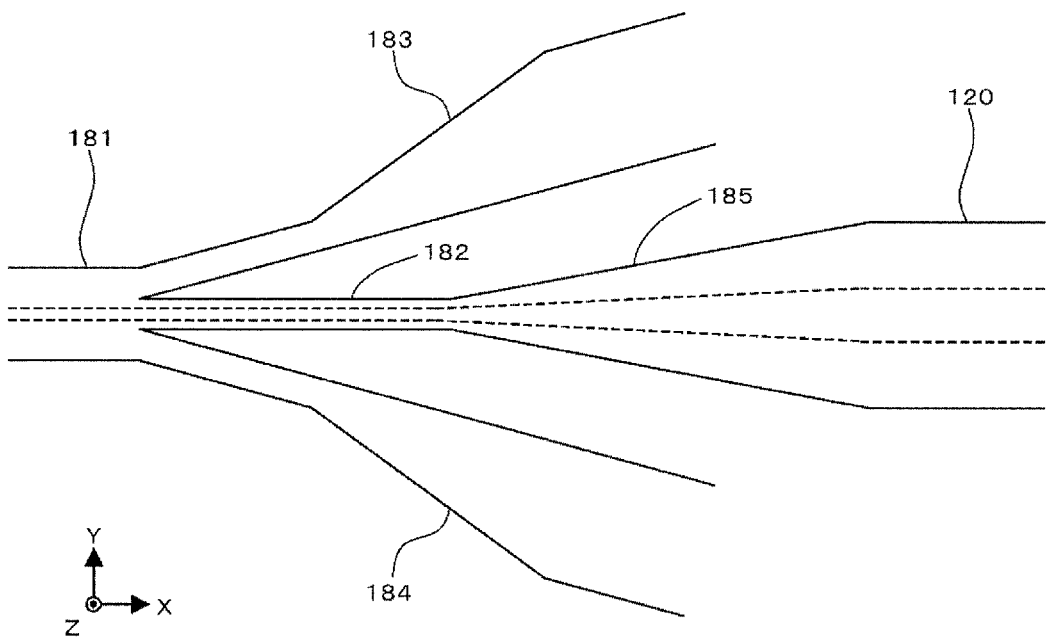

As shown in FIGS. 23A and 23B, in Embodiment 15, a manner in which the twelfth flow path section 182, the thirteenth flow path section 183, and the fourteenth flow path section 184 branch is different from a manner in which the third flow path section 130, the fourth flow path section 140, and the fifth flow path section 150 branch. After branching of the twelfth flow path section 182, the thirteenth flow path section 183, and the fourteenth flow path section 184, the flow path sections each having a constant cross-sectional shape are continued. In FIGS. 23A and 23B, dotted lines represent a region in which the measurement sample 12 flows.

Since the twelfth flow path section 182, the thirteenth flow path section 183, and the fourteenth flow path section 184 are thus branched, the length of the twelfth flow path section 182, and the length of the range L1 of each of the thirteenth flow path section 183 and the fourteenth flow path section 184 are changed in designing for fluid, whereby a relative ratio in resistance between: the twelfth flow path section 182; and flow path sections in the ranges L1 of the thirteenth flow path section 183 and the fourteenth flow path section 184 can be easily adjusted and changed. As a result, advantageously, the flow speed in the twelfth flow path section 182 can be easily adjusted to an appropriate value.

The branching flow path sections that branch from the intermediate flow path section may be provided at a plurality of stages in the X-axis direction. For example, preceding the eleventh flow path section 181, a sixteenth flow path section 186, a seventeenth flow path section 187, and a twentieth flow path section 190 may be added as the intermediate flow path section, and an eighteenth flow path section 188 and a nineteenth flow path section 189 may be added as the branching flow path sections, as shown in FIG. 24.

Figure 24:
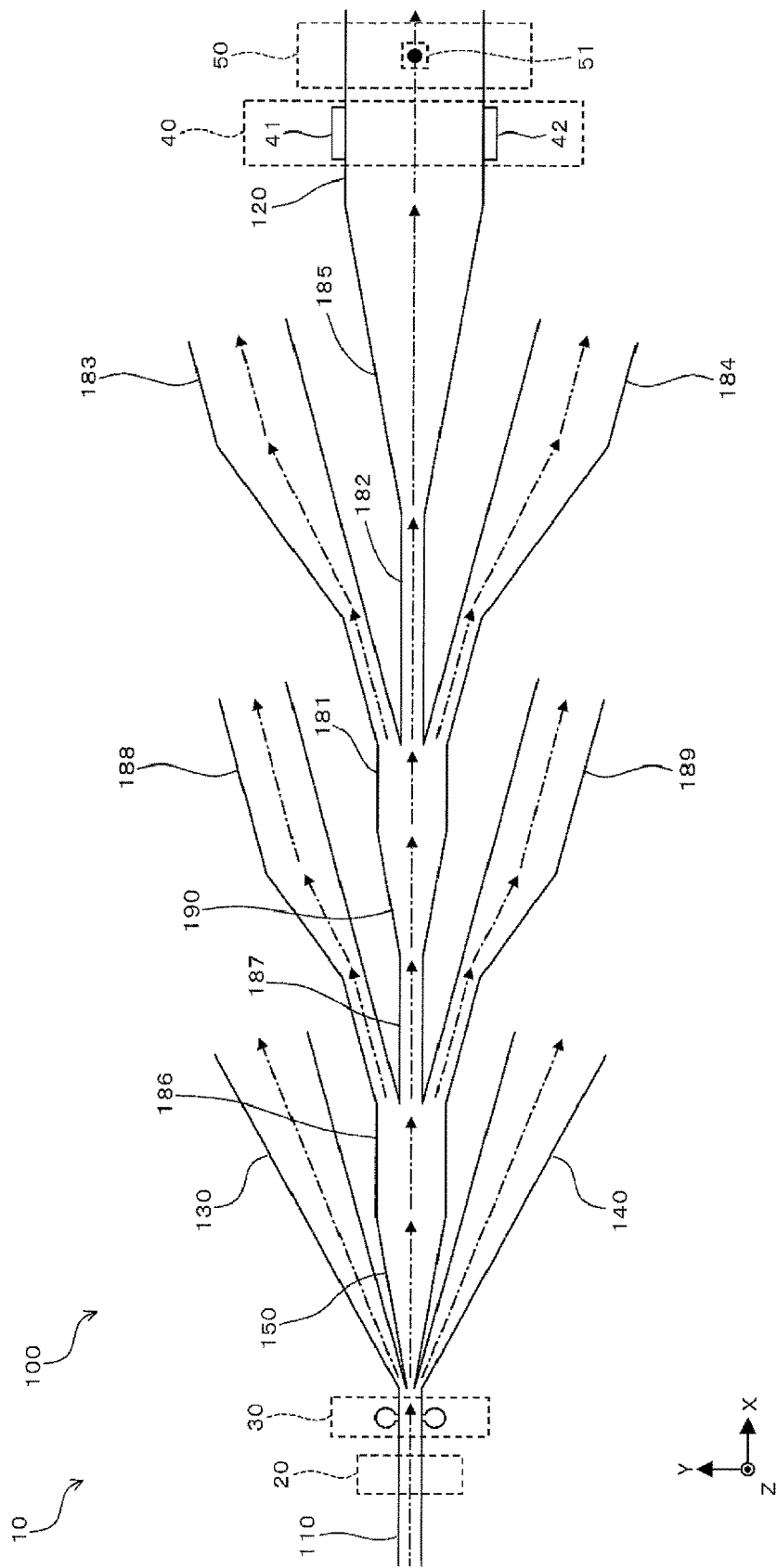
FIG. 24 is a schematic diagram illustrating a configuration of a particle imaging apparatus according to modification of Embodiment 15 as viewed in the Z-axis negative direction.

In FIG. 24, the sixteenth flow path section 186, the seventeenth flow path section 187, the eighteenth flow path section 188, the nineteenth flow path section 189, and the twentieth flow path section 190 have the same configurations as the eleventh flow path section 181, the twelfth flow path section 182, the thirteenth flow path section 183, the fourteenth flow path section 184, and the fifteenth flow path section 185, respectively. The length, the width, and the degree of expansion of each of the sixteenth flow path section 186, the seventeenth flow path section 187, the eighteenth flow path section 188, the nineteenth flow path section 189, and the twentieth flow path section 190 can be adjusted as appropriate. The sixteenth flow path section 186 may be set so as to be very short, or the sixteenth flow path section 186 may be omitted.

In the configuration shown in FIG. 24, the flow speed in the second flow path section 120 can be further reduced due to the sixteenth flow path section 186, the seventeenth flow path section 187, the eighteenth flow path section 188, the nineteenth flow path section 189, and the twentieth flow path section 190. Therefore, even when the speed at which a particle flows in the first flow path section 110 is further increased in order to extract an imaging target particle from a lot of particles faster, the speed at which the particle flows in the second flow path section 120 is significantly reduced, whereby the particle imaging unit 50 is allowed to take an accurate image of the particle.

Thus, in a case where the branching flow path sections are provided at a plurality of stages in the X-axis direction, the twelfth flow path section 182 and the fifteenth flow path section 185 may be omitted, and the eleventh flow path section 181 may be connected directly to the second flow path section 120 as shown in FIG. 25. In this case, the width of the second flow path section 120 is reduced as compared to that in FIG. 23B. In this configuration, the thirteenth flow path section 183 and the fourteenth flow path section 184 each have a width increased on the downstream side, whereby flowing in the thirteenth flow path section 183 and the fourteenth flow path section 184 is facilitated as compared to the second flow path section 120. Therefore, the flow rate of flow into the second flow path section 120 is reduced, and the flow speed in the second flow path section 120 can be reduced as compared to the flow speed in the eleventh flow path section 181.

In the configuration shown in FIG. 25, the width W1 of the second flow path section 120 can be significantly reduced. Therefore, the particles are less likely to deviate from an imaging range in the second flow path section 120. Therefore, as shown in FIG. 25, the particle alignment unit 40 can be omitted. When the particles deviate from the imaging range, the particle alignment unit 40 may be provided in the second flow path section 120 as appropriate. In this case, since the width W1 of the second flow path section 120 is narrow, acoustic force of the particle alignment unit 40 can be more effectively applied to particles.

Also in the configuration shown in FIG. 24 and FIG. 25, the particle alignment unit 40 may be provided in both or one of the eleventh flow path section 181 and the sixteenth flow path section 186.

What is claimed is:
1. A particle imaging apparatus comprising:
a flow path comprising a first flow path section, a second flow path section connected downstream of the first flow path section, and a third flow path section that is branched from the first flow path section, between the first flow path section and the second flow path section, the flow path configured to cause a measurement sample including particles to flow;
a particle detection unit comprising a light source configured to apply light to a particle that flows in the first flow path section, and a light detector that receives light generated from the particle by application of the light;
a particle sorting unit configured to adjust a flow direction of the particle flowing in the first flow path section such that the flow direction is selected from among at least a direction toward the second flow path section and a direction toward the third flow path section, based on an intensity of the light received by the light detector; and
a particle imaging unit configured to take an image of a particle that flows in the second flow path section,
wherein the flow path is structured such that a cross-sectional area of the second flow path section is greater than a cross-sectional area of the first flow path section, and
the first flow path section and the second flow path section are disposed so as to be linearly aligned.
2. The particle imaging apparatus of claim 1, wherein the particle detection unit detects, as an imaging target of the particle imaging unit, at least one cell selected from the group consisting of a circulating tumor cell, a vascular endothelial cell, a vascular endothelial progenitor cell, a mesenchymal stem cell, a hematopoietic stem cell, and an antigen-specific T-cell that are included in the measurement sample.
3. The particle imaging apparatus of claim 1, wherein the flow path is structured such that a speed at which a particle flows in the second flow path section is lower than a speed at which the particle flows in the first flow path section.
4. The particle imaging apparatus of claim 1, wherein the flow path is structured such that a flow rate in the second flow path section is lower than or equal to ⅓ of a flow rate in the first flow path section.
5. The particle imaging apparatus of claim 1, wherein the flow path is structured such that a speed at which a particle flows in the second flow path section is lower than or equal to ¹/₁₀ of a speed at which the particle flows in the first flow path section.
6. The particle imaging apparatus of claim 1, wherein the flow path is structured such that a central axis of the first flow path section and a central axis of the second flow path section are aligned with each other.
7. The particle imaging apparatus of claim 1, wherein the particle sorting unit is configured to:
guide an imaging target particle so as to flow straight into the second flow path section without applying an external force to the imaging target particle, and
apply an external force to a particle other than imaging target particles, changes a direction in which the particle flows, and guides the particle into the third flow path section.

8. The particle imaging apparatus of claim 1, wherein the flow path further comprises a fourth flow path section that branches from the first flow path section, between the first flow path section and the second flow path section, and the third flow path section and the fourth flow path section are disposed so as to be symmetric about a central axis of the first flow path section.

9. The particle imaging apparatus of claim 1, wherein the third flow path section has a cross-sectional area that increases from an upstream side of the flow path toward a downstream side thereof.

10. The particle imaging apparatus of claim 1, wherein the flow path is structured such that a flow rate in the second flow path section is reduced from a flow rate in the first flow path section due to the third flow path section, and a speed at which a particle flows in the second flow path section is thus made lower than a speed at which the particle flows in the first flow path section.

11. The particle imaging apparatus of claim 1, wherein the flow path is structured such that a cross-sectional area of the second flow path section is greater than a cross-sectional area of the first flow path section, and a speed at which a particle flows in the second flow path section is thus made lower than a speed at which the particle flows in the first flow path section.

12. The particle imaging apparatus of claim 1, wherein the flow path further comprises: an intermediate flow path section that connects between the first flow path section and the second flow path section; and a branching flow path section that branches from the intermediate flow path section.

13. The particle imaging apparatus of claim 12, wherein the flow path comprises a plurality of the branching flow path sections, and the plurality of the branching flow path sections are disposed so as to be symmetric about a central axis of the intermediate flow path section.

14. The particle imaging apparatus of claim 12, wherein the intermediate flow path section comprises a flow path section having a cross-sectional area increased toward the downstream side, on a side downstream of a position at which the branching flow path section branches, and the branching flow path section comprises a flow path section having a cross-sectional area increased toward the downstream side.

15. The particle imaging apparatus of claim 1, wherein the flow path comprises an intermediate flow path section that connects between the first flow path section and the second flow path section, and the intermediate flow path section comprises: a plurality of expanded flow path sections each having a cross-sectional area increased toward the downstream side; and a flow path section having a constant cross-sectional area and disposed between a plurality of the expanded flow path sections.

16. The particle imaging apparatus of claim 12, wherein the intermediate flow path section comprises a particle alignment unit that aligns particles in a flow direction.

17. The particle imaging apparatus of claim 1, wherein the imaging unit applies light to an imaging region in the second flow path section and receives light from the imaging region, and takes an image of the particle that flows in the imaging region.

18. The particle imaging apparatus of claim 1, wherein the particle imaging unit is a TDI camera.

19. A particle imaging method comprising:
causing a measurement sample to flow in a flow path which comprises a first flow path section, a second flow path section connected downstream of the first flow path section, and a third flow path section that is branched from the first flow path section, between the first flow path section and the second flow path section, the flow path being structured such that a cross-sectional area of the second flow path section is greater than a cross-sectional area of the first flow path section, and the first flow path section and the second flow path section are linearly aligned;
applying light to a particle in the measurement sample that flows at a first speed, and detecting light generated from the particle;
adjusting a direction in which the particle in the measurement sample flows, based on an intensity of the detected light; and
taking an image of a particle in the measurement sample that flows in the second flow path section at a second speed lower than the first speed.

20. A particle imaging apparatus comprising:
a flow path comprising a first flow path section, a second flow path section connected downstream of the first flow path section, and a third flow path section that is branched from the first flow path section, between the first flow path section and the second flow path section, the flow path configured to cause a measurement sample including particles to flow, and the first flow path section and the second flow path section are linearly aligned;
a particle detection unit comprising a light source that applies light to a particle that flows in the first flow path section, and a light detector that receives light generated from the particle by application of the light;
a particle sorting unit configured to adjust a flow direction of the particle flowing in the first flow path section such that the flow direction is selected from among at least a direction toward the second flow path section and a direction toward the third flow path section, based on an intensity of the light received by the light detector; and
a particle imaging unit configured to take an image of a particle that flows in the second flow path section,
wherein the third flow path section has a cross-sectional area that increases from an upstream side of the flow path toward a downstream side thereof.

* * * * *